(12) United States Patent
Burns et al.

(10) Patent No.: US 7,413,866 B2
(45) Date of Patent: Aug. 19, 2008

(54) COMPOSITIONS AND METHODS FOR DETECTING AND TREATING DISEASES AND CONDITIONS RELATED TO CHEMOKINE RECEPTORS

(75) Inventors: Jennifer M. Burns, San Mateo, CA (US); Zhenhua Miao, San Jose, CA (US); Zheng Wei, Redwood City, CA (US); Maureen C. Howard, Los Altos, CA (US); Brett A. Premack, San Carlos, CA (US); Thomas J. Schall, Palo Alto, CA (US)

(73) Assignee: ChemoCentryx, Inc., Mountain View, CA (US)

(*) Notice: Subject to any disclaimer, the term of this patent is extended or adjusted under 35 U.S.C. 154(b) by 693 days.

(21) Appl. No.: 10/452,015

(22) Filed: May 30, 2003

(65) Prior Publication Data

US 2004/0018563 A1    Jan. 29, 2004

Related U.S. Application Data

(63) Continuation-in-part of application No. 10/245,850, filed on Sep. 16, 2002.

(60) Provisional application No. 60/338,100, filed on Nov. 30, 2001, provisional application No. 60/337,961, filed on Nov. 30, 2001.

(51) Int. Cl.
    *G01N 33/50*   (2006.01)
    *C07K 14/00*   (2006.01)

(52) U.S. Cl. .................................. 435/7.2; 530/350

(58) Field of Classification Search ..................... None
    See application file for complete search history.

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen et al. | |
| 4,927,838 A | 5/1990 | Guthrie et al. | |
| 5,994,519 A | 11/1999 | Osbourn et al. | |
| 6,084,075 A | 7/2000 | Lind et al. | |
| 6,140,064 A | 10/2000 | Loetscher et al. | |
| 6,156,520 A | 12/2000 | Inglese et al. | |
| 6,180,336 B1 | 1/2001 | Osbourn et al. | |
| 6,184,358 B1 | 2/2001 | Loetscher et al. | |
| 6,329,159 B1 | 12/2001 | Andrew et al. | |
| 6,365,356 B1 | 4/2002 | Gershengorn | |
| 6,448,054 B1 | 9/2002 | Poznansky et al. | |
| 6,537,764 B1 | 3/2003 | Gerard et al. | |
| 6,699,677 B1 * | 3/2004 | Schall et al. | 435/7.24 |
| 2002/0004215 A1 | 1/2002 | Osbourn et al. | |
| 2002/0018776 A1 * | 2/2002 | Hancock | 424/145.1 |
| 2002/0025536 A1 | 2/2002 | Gyuris et al. | |
| 2002/0034757 A1 | 3/2002 | Cubicciotti | |
| 2002/0037539 A1 | 3/2002 | Qin et al. | |
| 2002/0048786 A1 | 4/2002 | Rosen et al. | |
| 2002/0061599 A1 | 5/2002 | Elling et al. | |
| 2002/0061834 A1 | 5/2002 | Rosen et al. | |
| 2002/0064770 A1 | 5/2002 | Nestor, Jr. et al. | |
| 2002/0076710 A1 | 6/2002 | Papsidero et al. | |

FOREIGN PATENT DOCUMENTS

| | | |
|---|---|---|
| EP | 0897980 A2 | 2/1999 |
| WO | WO 98/11218 A1 | 3/1998 |
| WO | WO 98/14480 A1 | 4/1998 |
| WO | WO 99/50461 A1 | 10/1999 |

OTHER PUBLICATIONS

Babcock, Gregory J. et al.; "Ligand Binding Characteristics of CXCR4 Incorporated into Paramagnetic Proteoliposomes"; *The Journal of Biological Chemistry* 2001, vol. 276 No. 42, pp. 38433-38440.

Baribaud, Frederic et al.; "Antigenically Distinct Conformations of CXCR4"; *Journal of Virology* 2001, vol. 75 No. 19, pp. 8957-8967.

Dairaghi, Daniel J.; "HHV8-encoded vMIP-1 Selectively Engages Chemokine Receptor CCR8"; *The Journal of Biological Chemistry* 1999, vol. 274, No. 31, pp. 21569-21574.

Dragic, Tatjana; "An overview of the determinants of CCR5 and CXCR4 co-reseptor function"; *Journal of General Virology* 2001, vol. 82, pp. 1807-1814.

Forster, Reinhold et al.; "Intracellular and Surface Expression of the HIV-1 Coreceptor CXCR4/Fusin on Various Leukocyte Subsets: Rapid Internalization and Recycling Upon Activation"; *The Journal of Immunology* 1998, vol. 160, pp. 1522-1531.

Gerlach, Lars Ole et al.; "Molecular Interactions of Cyclam and Bicyclam Non-peptide Antagonists with the CXCR4 Chemokine Receptor"; *The Journal of Biological Chemistry* 2001, vol. 276 No. 17, pp. 14153-14160.

Gosling, Jennifa et al.: "Cutting Edge: Identification of a Novel Chemokine Receptor That Binds Dendritic Cell- and T Cell-Active Chemokines Including ELC, SLC, and TECK"; *The Journal of Immunology* 2000, pp. 2851-2856.

Kledal, Thomas N. et al.; "A Broad-Spectrum Chemokine Antagonist Encoded by Kaposi's Sarcoma-Associated Herpesvirus"; *Science* 1997, vol. 277, pp. 1656-1659.

Lee, Benhur et al.; "Epitope Mapping of CCR5 Reveals Multiple Conformational States and Distinct but Overlapping Structures Involved in Chemokine and Coreceptor Function"; *The Journal of Biological Chemistry* 1999, vol. 274 No. 14, pp. 9617-9626.

Moepps, Barbara et al.; "Two murine homologues of the human chemokine receptor CXCR4 mediating stromal cell-derived factor 1α activation of $G_{i2}$ are differently expressed in vivo"; *Eur. J. Immunol.* 1997, vol. 27, pp. 2102-2112.

(Continued)

*Primary Examiner*—Marianne P. Allen
*Assistant Examiner*—Regina M DeBerry
(74) *Attorney, Agent, or Firm*—Townsend and Townsend and Crew LLP

(57) ABSTRACT

The present invention provides methods for identifying an agent that specifically binds and/or modulates one topology of a chemokine receptor but not a second topology of the receptor. Such agents are useful as therapeutics for diseases or conditions associated with a particular chemokine receptor topology. Moreover, the agents are useful for detecting a particular topology of a chemokine receptor, thereby diagnosing disease or predisposition for a disease. In addition, the agents are useful for identifying and isolating cells that express a particular topology of a chemokine receptor.

2 Claims, 10 Drawing Sheets

OTHER PUBLICATIONS

Muller, Anja et al.; "Involvement of chemokine receptors in breast cancer metastasis"; *Nature* 2001, vol. 410, pp. 50-56.

Parolin, Cristina et al.; "Use of Murine CXCR-4 as a Second Receptor by Some T-Cell-Tropic Human Immunodeficiency Viruses"; *Journal of Virology* 1998, vol. 72 No. 2, pp. 1652-1656.

Wegner, Scott A. et al.; "Genomic Organization and Functional Characterization of the Chemokine Receptor CXCR4, a Major Entry Co-receptor for Human Immunodeficiency Virus Type 1"; 1998 *The Journal of Biological Chemistry* 1998 vol. 273 No. 8, pp. 4754-4760.

Yoshida, Tetsuya et al.; "Identification of Single C Motif-1/Lymphotactin Receptor XCR1"; *The Journal of Biological Chemistry* 1998, vol. 273 No. 26, pp. 16551-16554.

Abdel-Magid, Ahmed F. et al.; "Reductive Amination of Aldehydes and Ketones by Using Sodium Triacetoxyborohydride"; *Tetrahedron Lett.*, 1990, vol. 31, pp. 5595-5598.

Barney, Charlotte L. et al.; "A Convenient Synthesis of Hindered Amines and α-Trifluoromethylamines from Ketones"; *Tetrahedron Lett.*, 1990, vol. 31, pp. 5547-5550.

Bertolini, Francesco et al.; "Endostatin, an antiangiogenic drug, induces tumor stabilization after chemotherapy or anti-CD20 therapy in a NOD/SCID mouse model of human high-grade non-Hodgkin lymphoma"; *Blood*, 2000, vol. 96, No. 1, pp. 282-287.

Bertolini, Francesco et al.; "CXCR4 Neutralization, a Novel Therapeutic Approach for Non-Hodgkin's Lymphoma"; *Cancer Research*, 2002, vol. 62, pp. 3106-3112.

Gribble, Gordon, W. et al.; "Reactions of Sodium Borohydride in Acidic Media; XVI. N-Methylation of Amines with Paraformaldehyde/Trifluoroacetic Acid"; *Synthesis*, 1987, pp. 709-711.

Kevill, Dennis N. et al.; "Correlation of the Rates of Solvolysis of Allyl and Benzyl Arenesulphonates"; *Journal of Chemical Society Perkin Trans.*, 1984, vol. 2, pp. 717-720.

Lin, Engnian et al.; "Antiangiogenic gene therapy targeting the endothelium-specific receptor tyrosine kinase Tie2"; *Proc. Natl. Acad. Sci.* 1998, vol. 95, pp. 8829-8834.

Liotta, Lance A.; "An attractive force in metastasis"; *Nature*, 2001, vol. 410, pp. 24-25.

Mattson, Ronald J. et al.: "An Improved Method for Reductive Alkylation of Amines Using Titanium (IV) Isopropoxide and Sodium Cyanoborohydride"; *J. Org. Chem.*, 1990, vol. 55, pp. 2552-2554.

Muller, Anja et al.; "Involvement of chemokine receptors in breast cancer metastasis"; *Nature*, 2001, vol. 410, pp. 50-56.

Neises, Bernhard et al.; "Simple Method for the Esterification of Carboxylic Acids"; *Angew. Chem. Int. Ed. Engl.*, 1978, vol. 17, No. 7, pp. 522-524.

Neote, Kuldeep, et al.; "Molecular Cloning, Functional Expression, and Signaling Characteristics of C-C Chemokine Receptor"; *Cell*, 1993, vol. 72, pp. 415-425.

Oppenheim, Joost J. et al.; "Properties of the Novel Proinflammatory Supergene "Intercrine" Cytokine Family"; *Annu. Rev. Immunol.*, 1991, vol. 9, pp. 617-648.

Ponath, Paul D. et al.; "Molecular Cloning and Characterization of a Human Eotaxin Receptor Expressed Selectively on Eosinophils"; *J. Exp. Med.*, 1996, vol. 183, pp. 2437-2448.

Power, Christine A. et al.; "Molecular Cloning and Functional Expression of a Novel CC Chemokine Receptor cDNA from a Human Basophilic Cell Lines"; *The Journal of Biological Chemistry*, 1995, vol. 270, No. 33, pp. 19495-19500.

Pulaski, Beth A. et al.; "Cooperativity of *Staphylococcal aureus* Enterotoxin B Superantigen, Major Histocompatibility Complex Class II, and CD80 for Immunotherapy of Advanced Spontaneous Metastases in a Clinically Relevant Postoperative Mouse Breast Cancer Model": *Cancer Research*, 2000, vol. 60, pp. 2710-2715.

Schall, Thomas J.; "Biology of the Rantes/sis Cytokine Family"; *Cytokine*, 1996, vol. 3, No. 3, pp. 165-183.

Watanabe, Yoshihisa et al.; "The Selective Amination of Carbonyl Compounds using Iron Pentacarbonyl"; *Tetrahedron Lett.*, 1974, vol. 22, pp. 1879-1880.

Ebert, Lisa M. et al.; "Coregulation of CXC Chemokine Receptor and CD4 Expression on T Lymphocytes During Allogeneic Activation"; 2001, *Journal of Immunology*, vol. 166, No. 8, pp. 4870-4878.

* cited by examiner

Figure 6

|  | Clone #1 | Clone #2 | Clone #3 | Clone #4 | Clone #5 |
|---|---|---|---|---|---|
| HEK293-CCR1 | +++ | ++ | +++ | + | +++ |
| THP-1 | ++ | + | + | ++ | + |
| Monocytes | ++ | - | + | - | - |
| Neutrophils | ++ | ++ | - | - | ++ |
| Immature DC | ++ | + | + | - | + |
| NSO-CCR1 | + | + | + | ++ | ++ |

Legend:
-     no reactivity
+     weak reactivity
++     moderate reactivity
+++     strong reactivity

Figure 7

$^{125}$I MIP-1 α Binding Summary

|  | HEK293-CCR1 | THP-1 | Monocytes | Neutrophils | NSO-CCR1 |
|---|---|---|---|---|---|
| CKβ8(1-99) | 64 nM | 6.3 nM | 10.3 nM | n/a | 3.9 nM |
| CKβ8(25-99) | 1.34 nM | 0.27 nM | 0.25 nM | n/a | 0.02 nM |
| Leukotactin | < 0.2 nM | < 0.2 nM | < 0.2 nM | n/a | 0.02 nM |
| MIP1 α | 0.54 nM | 0.17 nM | 0.27 nM | n/a | 0.15 nM |

Note: $^{125}$I MIP1 α does not bind to neutrophils

Figure 8

| | THP-1 | | | Monocytes | | | Neutrophils | | | Immature DC | | |
|---|---|---|---|---|---|---|---|---|---|---|---|---|
| | 1 nM | 10 nM | 100 nM | 1 nM | 10 nM | 100 nM | 1 nM | 10 nM | 100 nM | 1 nM | 10 nM | 100 nM |
| CKβ8(1-99) | | | | | | | | | | | | |
| CKβ8(25-99) | nt | nt | nt | | | | | | | nt | nt | nt |
| Leukotactin | | | | | | | | | | | | |
| MIP1 α | | | | | | | | | | | | |
| mMIP1 γ | | | | | | | | | | | | |

Notes: Color represents the Migration Index.
1. Black: Index<1.5; gray: Index at 1.5 -4.9; White: Index at 5.0-9.9
2. Leukotactin is very potent CCR1 agonist. It can induce CCR1-mediated cell migration at sub-nM concentrations.

Figure 9

|  | HEK293-CCR1 | | | THP-1 | | | Monocytes | | | Neutrophils | | | Immature DC | | |
|---|---|---|---|---|---|---|---|---|---|---|---|---|---|---|---|
|  | 1 nM | 10 nM | 100 nM | 1 nM | 10 nM | 100 nM | 1 nM | 10 nM | 100 nM | 1 nM | 10 nM | 100 nM | 1 nM | 10 nM | 100 nM |
| CKβ8(1-99) | + | ++ | +++ | + | ++ | +++ | - | + | ++ | - | - | - |  |  | ++ |
| CKβ8(25-99) | ++ | +++ | +++ | ++ | +++ | +++ | + | ++ | ++ | - | - | weak |  |  | ++ |
| Leukotactin | ++ | +++ | +++ | + | +++ | +++ | + | ++ | ++ | - | weak | + |  | ++ | ++ |
| MIP1 α | ++ | +++ | +++ | + | ++ | +++ | + | ++ | ++ | - | - | - |  | ++ | ++ |
| mMIP1 γ | - | ++ | +++ | - | + | ++ | - | + | ++ | - | - | - |  |  | ++ |

Legend:
-     -    no reactivity
-     +    weak reactivity
-    ++   moderate reactivity
-   +++   strong reactivity

Figure 10

|  | Clone #1 | Clone #2 | Clone #3 | Clone #4 | Clone #5 |
|---|---|---|---|---|---|
| HEK-293 CCR1 | +++ | ++ | +++ | + | +++ |
| Jurkat CCR1 | ++ | - | + | - | - |

Legend:
-    no reactivity
+    weak reactivity
++   moderate reactivity
+++  strong reactivity

COMPOSITIONS AND METHODS FOR DETECTING AND TREATING DISEASES AND CONDITIONS RELATED TO CHEMOKINE RECEPTORS

CROSS-REFERENCES TO RELATED APPLICATIONS

The present application is a continuation-in-part of U.S. application Ser. No. 10/245,850, filed Sep. 16, 2002, which claims priority to U.S. Patent Application Ser. No. 60/338,100, filed Nov. 30, 2001 and U.S. Ser. No. 60/337,961, filed Nov. 30, 2001, each of which is explicitly incorporated herein by reference in its entirety and for all purposes.

BACKGROUND OF THE INVENTION

Chemokines constitute a family of small cytokines that are produced in inflammation and regulate leukocyte recruitment (Baggiolini, M. et al., *Adv. Immunol.* 55: 97-179 (1994); Springer, T. A., *Annu. Rev. Physiol.* 57: 827-872 (1995); and Schall, T. J. and K. B. Bacon, *Curr. Opin. Immunol.* 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, including T cells and B cells. In addition to stimulating chemotaxis, other changes can be selectively induced by chemokines in responsive cells, including changes in cell shape, transient rises in the concentration of intracellular free calcium ions ($Ca^{2+}$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

Two subfamilies of chemokines, designated as CXC and CC chemokines, are distinguished by the arrangement of the first two of four conserved cysteine residues, which are either separated by one amino acid (as in CXC chemokines SDF-1, IL-8, IP-10, MIG, PF4, ENA-78, GCP-2, GROα, GROβ, GROγ, NAP-2, NAP-4) or are adjacent residues (as in CC chemokines MIP-1α, MIP-1β, RANTES, MCP-1, MCP-2, MCP-3, I-309). Most CXC chemokines attract neutrophil leukocytes. For example, the CXC chemokines interleukin 8 (IL-8), platelet factor 4 (PF4), and neutrophil-activating peptide 2 (NAP-2) are potent chemoattractants and activators of neutrophils. The CXC chemokines designated MIG (monokine induced by gamma interferon) and IP-10 (interferon-γ inducible 10 kDa protein) are particularly active in inducing chemotaxis of activated peripheral blood lymphocytes. CC chemokines are generally less selective and can attract a variety of leukocyte cell types, including monocytes, eosinophils, basophils, T lymphocytes and natural killer cells. CC chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

CC and CXC chemokines act through receptors that belong to a superfamily of seven transmembrane spanning G protein-coupled receptors (Murphy, P. M., *Pharmacol Rev.* 52:145-176 (2000)). This family of G-protein coupled receptors comprises a large group of integral membrane proteins, containing seven transmembrane-spanning regions. The receptors are coupled to G proteins, which are heterotrimeric regulatory proteins capable of binding GTP and mediating signal transduction from coupled receptors, for example, by the production of intracellular mediators.

Generally speaking, chemokine and chemokine receptor interactions tend to be promiscuous in that one chemokine can bind many chemokine receptors and conversely a single chemokine receptor can interact with several chemokines. There are a few exceptions to this rule; one such exception has been the interaction between SDF-1 and CXCR4 (Bleul et al., *J Exp Med*, 184(3): 1101-9 (1996); Oberlin et al., *Nature*, 382(6594): 833-5 (1996)). Originally identified as a pre-B cell growth-stimulating factor (Nagasawa et al., *Proc Natl Acad Sci USA*, 91(6): 2305-9 (1994)), SDF-1 has been the only reported human ligand for CXCR4. The SDF-1 gene encodes two proteins, designated SDF-1α and SDF-1β, by alternative splicing. These two proteins are identical except for the four amino acid residues that are present in the carboxy-terminus of SDF-1β and absent from SDF-1α.

The SDF-1/CXCR4 chemokine/chemokine receptor pair has been implicated as an important mediator of normal embryonic development as well as several disease states. Gene knockout data for both CXCR4 and SDF-1 demonstrate that the deletion of either this receptor or ligand proves to be embryonic lethal (Loetscher et al., *J Biol Chem*, 269(1): 232-7 (1994); Ma et al., *Proc Natl Acad Sci U S A*, 95(16): 9448-53 (1998); Zou et al., *Nature*, 393(6685): 595-9 (1998)). Additionally, this ligand/receptor pair plays a role in HIV infection (Bleul et al., *Nature*, 382(6594): 829-33 (1996); Deng et al., *Nature*, 381(6584): 661-6 (1996); Feng et al., *Science*, 272(5263): 872-7 (1996)), and has linked to HIV pathogenesis. CXCR4 can induce apoptosis and this pathway can be inhibited by SDF-1 (Berndt et al., *Proc Natl Acad Sci U S A*, 95(21): 12556-61 (1998)), thus further supporting the evidence that SDF-1 and CXCR4 are a closely linked chemokine/chemokine receptor pair.

Most recently, SDF-1 and CXCR4 have been implicated as potentially playing a role in breast cancer metastasis (Muller et al., *Nature*, 410(6824): 50-6 (2001)). CXCR4 expression was detected on breast tumor cells, while elevated levels of SDF-1 were identified in the organs of metastatic growth such as lymph node, lung, liver and bone marrow, but not in other organs where tumors were not detected. Furthermore, this metastatic growth could be inhibited by the addition of anti-CXCR4, supporting the hypothesis that this ligand receptor pair has a role in tumor metastasis.

The CCR1 gene encodes a member of the beta or CC chemokine receptor family comprising 354 amino acids with predicted seven transmembrane topology (Neote, K et al. *Cell* 72:415-425 (1993)). The ligands of this receptor include MIP-1α, RANTES, MCP-3 and MPIF-1. CCR1 receptors are widely expressed on human leukocytes, can mediate G protein signal transduction, and are critical for the recruitment of effector immune cells to sites of inflammation and infection. Human CCR1 protein (SEQ ID NO:2) is antigenic in mice and specific mouse-anti human CCR1 monoclonal antibodies are widely available (R&D Systems, Pharmingen). Knockout studies of the mouse homolog suggest roles of this gene in host protection from inflammatory response, regulation of susceptibility to virus and parasites as well as roles in transplant rejection and tolerance. This gene and other chemokine receptor genes, including CCR2, CCR3, CCR5 are found to form a gene cluster on human chromosome 3p21 (Murphy, P. M., *Pharmacol Rev.* 52:145-176 (2000)).

There are many aspects of chemokine receptor signaling and selectivity for ligands that were not previously understood. The present invention addresses these and other issues.

BRIEF SUMMARY OF THE INVENTION

The present invention provides methods of identifying an agent that binds to a chemokine receptor having a first topology but does not bind to a chemokine receptor having a second topology. In some embodiments, the methods comprise i. providing a first cell comprising a chemokine receptor having a first topology and a second cell comprising a chemokine receptor having a second topology, wherein:
   a. the chemokine receptor having the first topology binds to a first and a second chemokine,
   b. the first and second chemokines compete for binding to the chemokine receptor having the first topology, and
   c. the chemokine receptor having the second topology binds to the first but not the second chemokine;

ii. contacting an agent of less than 1,500 daltons to the chemokine receptors; and iii. selecting an agent that binds to the first topology of the chemokine receptor but does not bind to a chemokine receptor having a second topology.

In some embodiments, the agent is less than 600 daltons.

In some embodiments, the receptor having the first topology binds SDF-1 and I-TAC and the receptor having the second topology binds to SDF-1 but not I-TAC. In some embodiments, the agent is selected by identifying an agent that competes with SDF-1 and I-TAC for binding to the receptor having the first topology.

In some embodiments, the method further comprises selecting an agent that modulates cell function. In some embodiments, the cell function is selected from the group consisting of apoptosis, cell growth, cell proliferation and cell migration. In some embodiments, the method further comprises selecting an agent that modulates intracellular signaling triggered by ligand binding to the first topology of the chemokine receptor, thereby identifying an agent that modulates intracellular signaling triggered by ligand binding to a chemokine receptor having a first topology but not the second topology.

In some embodiments, the chemokine receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, CXR1, CCXCKR (CCR11), FPRL1 (CCR12), US28, ECRF3, Kaposi's Sarcoma-associated Herpesvirus GPCR, Poxvirus membrane-bound G Protein-coupled receptors, D6, and DARC.

In some embodiments, the first cell or the second cell is a cancer cell. In some embodiments, the cancer cell is selected from the group consisting of a breast cancer cell, an ovarian cancer cell, cervical cancer cell, a Burkitt's lymphoma cell and a glioblastoma cell. In some embodiments, the first cell or the second cell is a neutrophil, monocyte, macrophage, eosinophil, basophil, mast cell, dendritic cell, hematopoietic stem cell, platelet or B cell.

In some embodiments, the first cell or the second cell does not support an HIV infection. In some embodiments, the first cell or the second cell is not a T-cell. In some embodiments, the agent competes for binding with a natural ligand of the chemokine receptor. In some embodiments, the method further comprising selecting an agent that modulates a cell or tissue response in an animal, thereby identifying an agent that modulates a chemokine receptor-mediated tissue or cell response in an animal.

In some embodiments, the cell or tissue response comprises chemotaxis of cells. In some embodiments, the chemotactic cells are leukocytes. In some embodiments, leukocyte chemotaxis is decreased. In some embodiments, leukocyte chemotaxis is increased. In some embodiments, the cell or tissue response comprises the development of cancer. In some embodiments, the cell or tissue comprises cancer cells. In some embodiments, the cell or tissue response comprises inflammation. In some embodiments, the agent decreases cancer when a therapeutically sufficient amount of the agent is administered to an animal having cancer.

The present invention also provides agents that bind to a chemokine receptor having a first topology but does not bind to the chemokine receptor having a second topology wherein the agent is identified by the above-listed method.

The present invention also provides methods of determining the presence or absence of a cell. In some embodiments, the methods comprise determining the presence or absence of a chemokine receptor in a tissue sample by contacting the tissue sample with an agent identified by the method of claim 1, thereby determining the presence or absence of the cell. In some embodiments, the cell is a cancer cell.

The present invention also provides methods of identifying an antibody that binds to a chemokine receptor having a first topology but does not bind to a chemokine receptor having a second topology. In some embodiments, the methods comprise i. providing a first cell comprising a chemokine receptor having a first topology and a second cell comprising a chemokine receptor having a second topology wherein:
   a. the chemokine receptor having the first topology binds to a first and a second chemokine,
   b. the first and second chemokines compete for binding to the chemokine receptor having the first topology, and
   c. the chemokine having the second topology binds to the first but not the second chemokine;;

ii. contacting an antibody to the chemokine receptors; and iii. selecting an antibody that binds to the first topology of the chemokine receptor but does not bind to a chemokine receptor having a second topology.

In some embodiments, the method further comprises selecting an antibody that modulates cell function. In some embodiments, the receptor having the first topology binds SDF-1 and I-TAC and the receptor having the second topology binds to SDF-1 but not I-TAC. In some embodiments, the antibody is selected by identifying an agent that competes with SDF-1 or I-TAC for binding to the receptor having the first topology.

In some embodiments, the cell function is selected from the group consisting of apoptosis, cell growth, cell proliferation and cell migration. In some embodiments, the method further comprises selecting an antibody that modulates intracellular signaling triggered by ligand binding to the first topology of the chemokine receptor, thereby identifying an antibody that modulates intracellular signaling triggered by ligand binding to a chemokine receptor having a first topology but not the second topology.

In some embodiments, the chemokine receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, CXR1, CCXCKR (CCR11), FPRL1 (CCR12), US28, ECRF3, Kaposi's Sarcoma-associated Herpesvirus GPCR, Poxvirus membrane-bound G Protein-coupled receptors, D6, and DARC. In some embodiments, the first cell or the second cell is a cancer cell. In some embodiments, the cancer cell is selected from the group consisting of a breast cancer cell, an ovarian cancer cell, cervical cancer cell, a Burkitt's lymphoma cell and a glioblastoma cell.

In some embodiments, the first cell or the second cell is a neutrophil, monocyte, macrophage, eosinophil, basophil, mast cell, dendritic cell, hematopoietic stem cell, platelet or B cell. In some embodiments, the first cell or the second cell does not support an HIV infection. In some embodiments, the first cell or the second cell is not a T-cell.

In some embodiments, the antibody competes for binding with a natural ligand of the chemokine receptor. In some embodiments, the method further comprises selecting an antibody that modulates a cell or tissue response in an animal, thereby identifying an antibody that modulates a chemokine receptor-mediated tissue or cell response in an animal.

In some embodiments, the cell or tissue response comprises chemotaxis of cells. In some embodiments, the chemotactic cells are leukocytes. In some embodiments, leukocyte chemotaxis is decreased. In some embodiments, leukocyte chemotaxis is increased. In some embodiments, the cell or tissue response comprises the development of cancer. In some embodiments, the cell or tissue comprises cancer cells. In some embodiments, the cell or tissue response comprises inflammation. In some embodiments, the antibody decreases cancer when a therapeutically sufficient amount of the agent is administered to an animal having cancer.

The present invention also provides antibodies that bind to a chemokine receptor having a first topology but does not bind to the chemokine receptor having a second topology identified by the above-listed method.

The present invention also provides a method of determining the presence or absence of a cell. In some embodiments, the methods comprise determining the presence or absence of a chemokine receptor in a tissue sample by contacting the tissue sample with an antibody identified by the above-listed method, thereby determining the presence or absence of the cell. In some embodiments, the cell is a cancer cell.

The present invention also provides methods of identifying a novel topologyies of a chemokine receptor. In some embodiments, the methods comprise providing at least two cell types, each cell type expressing a chemokine receptor;

testing a plurality of different chemokines for the ability to bind to the chemokine receptor on each of the two cell types; and identifying a first chemokine that binds to the chemokine receptor on a first cell type but does not bind to the chemokine receptor on a second cell type, wherein:

the chemokine receptor on the first cell type binds to a first and a second chemokine, and the first and second chemokines compete for binding to the chemokine receptor on the first cell type, thereby identifying novel topologies of a chemokine receptor.

In some embodiments, the at least two cell types express the same chemokine receptor. In some embodiments, the chemokine receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, CXR1, CCXCKR (CCR11), FPRL1 (CCR12), US28, ECRF3, Kaposi's Sarcoma-associated Herpesvirus GPCR, Poxvirus membrane-bound G Protein-coupled receptors, D6, and DARC.

In some embodiments, the plurality of different chemokines comprise ITAC and SDF-1, wherein a first cell type comprises a chemokine receptor with a first topology on which ITAC and SDF-1 compete for binding and, wherein a second cell type comprises a chemokine receptor with a second topology on which ITAC and SDF-1 do not compete for binding.

In some embodiments, at least 3 cell types are tested. In some embodiments, at least 10 chemokines are tested.

In some embodiments, the chemokines are selected from the group consisting of CL1, XCL2, CX3CL1, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28. In some embodiments, the chemokines are tethered to a solid support.

In some embodiments, the testing step comprises determining the ability of the chemokines to compete with a ligand that binds to the chemokine receptor in each cell type. In some embodiments, the ligand is labeled. In some embodiments, at least one cell type expresses an endogenous chemokine receptor. In some embodiments, at least one cell type expresses a recombinantly expressed chemokine receptor. In some embodiments, the cell types tested comprise a cancer cell and a non-cancer cell.

The present invention also provides methods of detecting a first topology of a chemokine receptor in a sample. In some embodiments, the methods comprise contacting the sample with the an agent that specifically binds to a chemokine receptor in having a first topology but not a chemokine receptor having a second topology; and detecting whether the agent binds to the sample, thereby detecting the first topology of the chemokine receptor.

The invention also provides methods of purifying cells that bind an agent specific for a first topology of a chemokine receptor having a first topology, but not a chemokine receptor having a second topology. In some embodiments, the methods comprise contacting a sample comprising cells to the agent; and selecting cells that bind to the agent.

The present invention also provides methods of identifying an agent that modulates binding of a non-viral pathogen to a cell. In some embodiments, the methods comprise (i) providing a first cell comprising a chemokine receptor having a first topology and a second cell comprising a chemokine receptor having a second topology; (ii) contacting an agent to the chemokine receptors; and (iii) selecting an agent that: (a) binds to the first topology of the chemokine receptor but not the chemokine receptor having the second topology, and (b) modulates binding of a non-viral pathogen to a cell.

The present invention also provides methods of identifying a cancer cell. In some embodiments, the methods comprise determining whether I-TAC and SDF-1 compete for binding on a chemokine receptor of a cell in the tissue sample, wherein competition for binding indicates the presence of a cancer cell.

In some embodiments, the cancer cell is selected from the group consisting of a breast cancer cell, an ovarian cancer cell, cervical cancer cell, a Burkitt's lymphoma cell and a glioblastoma cell.

The present invention also provides kits for detecting I-TAC binding to a chemokine receptor that binds SDF-1 and I-TAC, the kit comprising, chemokines I-TAC and SDF-1, wherein at least one of the chemokines is labeled; and a solid support or receptacle for measuring chemokin-chemokine receptor binding.

The present invention also provides methods of identifying an agent that modulates viral binding to a chemokine receptor having a first topology but not a chemokine receptor having not a second topology. In some embodiments, the methods comprise:

(i) providing a first cell comprising a chemokine receptor in the first confirmation and a second cell comprising a chemokine receptor having a second topology wherein:
  a. the chemokine receptor having the first topology binds to a first and a second chemokine,
  b. the first and second chemokines compete for binding to the chemokine receptor having the first topology, and
  c. the chemokine receptor having the second topology binds to the first but not the second chemokine;
(ii) contacting an agent to the chemokine receptors; and
(iii) selecting an agent that (a) binds to the first topology of the chemokine receptor having the first topology but not the chemokine receptor having the second topology, and (b) modulates viral binding to a chemokine receptor, thereby identifying an agent that modulates viral binding to a chemokine receptor having the first topology but not the chemokine receptor having a second topology.

The present invention also provides methods of identifying an agent that binds to a chemokine receptor having a first topology but does not bind to the chemokine receptor having a second topology. In some aspects, the methods comprise: i. providing a first cell comprising a chemokine receptor having a first topology and a second cell comprising the chemokine receptor having a second topology; ii. contacting an agent of less than 1,500 daltons to the chemokine receptors; and iii. selecting an agent that binds to the first topology of the chemokine receptor but does not bind to a chemokine receptor having a second topology. In some aspects, the agent is less than 600 daltons.

In some aspects, the method further comprises selecting an agent that modulates cell function. In some aspects, the cell function is selected from the group consisting of apoptosis, cell growth, cell proliferation and cell migration.

In some aspects, the method further comprises selecting an agent that modulates intracellular signaling triggered by ligand binding to the first topology of the chemokine receptor, thereby identifying an agent that modulates intracellular signaling triggered by ligand binding to a chemokine receptor having a first topology but not the second topology. In some aspects, the agent modulates mobilization of intracellular calcium in response to binding of a ligand to the first topology of the chemokine receptor.

In some aspects, the chemokine receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, CXR1, CCXCKR (CCR11), FPRL1 (CCR12), US28, ECRF3, Kaposi's Sarcoma-associated Herpesvirus GPCR, Poxvirus membrane-bound G Protein-coupled receptors, D6, and DARC.

In some aspects, the first cell or the second cell is a cancer cell. In some aspects, the cancer cell is selected from the group consisting of a breast cancer cell, an ovarian cancer cell, cervical cancer cell, a Burkitt's lymphoma cell and a glioblastoma cell. In some aspects, the first cell or the second cell is a neutrophil, monocyte, macrophage, eosinophil, basophil, mast cell, dendritic cell, hematopoietic stem cell, platelet or B cell. In some aspects, the first cell or the second cell does not support an HIV infection. In some aspects, the first cell or the second cell is not a T-cell.

In some aspects, the agent competes for binding with a natural ligand of the chemokine receptor.

In some aspects, the method further comprises selecting an agent that modulates a cell or tissue response in an animal, thereby identifying an agent that modulates a chemokine receptor-mediated tissue or cell response in an animal. In some aspects, the cell or tissue response comprises chemotaxis of cells. In some aspects, the chemotactic cells are leukocytes. In some aspects, leukocyte chemotaxis is decreased. In some aspects, leukocyte chemotaxis is increased. In some aspects, the cell or tissue response comprises the development of cancer. In some aspects, the cell or tissue comprises cancer cells. In some aspects, the cell or tissue response comprises inflammation. In some aspects, the agent decreases cancer when a therapeutically sufficient amount of the agent is administered to an animal having cancer.

The invention also provides an agent identified by any of the methods provided above.

The invention also provides a method of identifying a cancer cell comprising determining whether the agent identified in the above-listed method binds to CXCR4 in a tissue sample, wherein binding of the agent to CXCR4 indicates the presence of cancer.

The present invention also provides methods of identifying a chemokine that binds to a chemokine receptor having a first topology but does not bind to the chemokine receptor having a second topology. In some aspects, the method comprises: i. providing a first cell comprising a chemokine receptor having a first topology and a second cell comprising the chemokine receptor having a second topology; ii. contacting the chemokine to the chemokine receptors; and iii. selecting a chemokine that binds to the first topology of the chemokine receptor but does not bind to the chemokine receptor having a second topology.

In some aspects, the chemokine modulates mobilization of intracellular calcium in response to binding of the chemokine to the first topology of the chemokine receptor. In some aspects, the chemokine receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, CXR1, CCXCKR (CCR11), FPRL1 (CCR12), FPRL1 (CCR12), US28, ECRF3, Kaposi's Sarcoma-associated Herpesvirus GPCR, Poxvirus membrane-bound G Protein-coupled receptors, D6, and DARC.

In some aspects, the first cell or the second cell is a cancer cell. In some aspects, the cancer cell is selected from the group consisting of a breast cancer cell, an ovarian cancer cell, cervical cancer cell, a Burkitt's lymphoma cell and a glioblastoma cell. In some aspects, the first cell or the second cell is a neutrophil, monocyte, macrophage, eosinophil, basophil, mast cell, dendritic cell, hematopoietic stem cell, platelet or B cell. In some aspects, the first cell or the second cell does not support an HIV infection. In some aspects, the first cell or the second cell is not a T-cell.

In some aspects, the method further comprises selecting a chemokine that modulates a cell or tissue response in an animal, thereby identifying a chemokine that modulates a chemokine receptor-mediated tissue or cell response in an animal. In some aspects, the cell or tissue response comprises chemotaxis of cells. In some aspects, the chemotactic cells are leukocytes. In some aspects, leukocyte chemotaxis is decreased. In some aspects, leukocyte chemotaxis is increased. In some aspects, the cell or tissue response comprises the development of cancer. In some aspects, the cell or tissue comprises cancer cells. In some aspects, the cell or tissue response comprises inflammation.

The present invention also provides method of identifying an antibody that binds to a chemokine receptor having a first topology but does not bind to a chemokine receptor having a second topology. In some aspects, the method comprises: i. providing a first cell comprising a chemokine receptor having a first topology and a second cell comprising the chemokine receptor having a second topology; ii. contacting an antibody to the chemokine receptors; and iii. selecting an antibody that binds to the first topology of the chemokine receptor but does not bind to a chemokine receptor having a second topology.

In some aspects, the method further comprises selecting an antibody that modulates cell function. In some aspects, the cell function is selected from the group consisting of apoptosis, cell growth, cell proliferation and cell migration.

In some aspects, the method further comprises selecting an antibody that modulates intracellular signaling triggered by ligand binding to the first topology of the chemokine receptor, thereby identifying an antibody that modulates intracellular signaling triggered by ligand binding to a chemokine receptor having a first topology but not the second topology. In some aspects, the antibody modulates mobilization of intracellular calcium in response to binding of a ligand to the first topology of the chemokine receptor. In some aspects, the chemokine receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, CXR1, CCXCKR (CCR11), FPRL1 (CCR12), US28, ECRF3, Kaposi's Sarcoma-associated Herpesvirus membrane-bound G Protein-coupled receptors, D6, and DARC.

In some aspects, the first cell or the second cell is a cancer cell. In some aspects, the cancer cell is selected from the group consisting of a breast cancer cell, an ovarian cancer cell, cervical cancer cell, a Burkitt's lymphoma cell and a glioblastoma cell. In some aspects, the first cell or the second cell is a neutrophil, monocyte, macrophage, eosinophil, basophil, mast cell, dendritic cell, hematopoietic stem cell, platelet or B cell. In some aspects, the first cell or the second cell does not support an HIV infection. In some aspects, the first cell or the second cell is not a T-cell. In some aspects, the antibody competes for binding with a natural ligand of the chemokine receptor.

In some aspects, the method further comprises selecting an antibody that modulates a cell or tissue response in an animal, thereby identifying an antibody that modulates a chemokine receptor-mediated tissue or cell response in an animal. In some aspects, the cell or tissue response comprises chemotaxis of cells. In some aspects, the chemotactic cells are leukocytes. In some aspects, leukocyte chemotaxis is decreased. In some aspects, leukocyte chemotaxis is increased. In some aspects, the cell or tissue response comprises the development of cancer. In some aspects, the cell or tissue comprises cancer cells. In some aspects, the cell or tissue response comprises inflammation. In some aspects, the antibody decreases cancer when a therapeutically sufficient amount of the agent is administered to an animal having cancer.

The invention also provides an antibody identified by the methods provided above.

The invention also provides a method of identifying a cancer cell comprising determining whether the antibody identified in the above-listed method binds to CXCR4 in a tissue sample, wherein binding of the antibody to CXCR4 indicates the presence of cancer.

The invention also provides methods of identifying novel topologies of a chemokine receptor. In some aspects, the method comprises, providing at least two cell types, each cell type expressing the chemokine receptor; testing a plurality of different chemokines for the ability to bind to the chemokine receptor on the two cell types; and identifying a chemokine that binds to the chemokine receptor on a first cell type but does not bind to the chemokine receptor on a second cell type, thereby identifying novel topologies of a chemokine receptor.

In some aspects, the chemokine receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, CXR1, CCX-CKR (CCR11), (CCR12), US28, ECRF3, Kaposi's Sarcoma-associated Herpesvirus GPCR, Poxvirus membrane-bound G Protein-coupled receptors, D6, and DARC.

In some aspects, the plurality of different chemokines comprise ITAC and SDF-1 and a first cell type comprises a topology of CXCR4 on which ITAC and SDF-1 compete for binding and a second cell type comprises a topology of CXCR4 on which ITAC and SDF-1 do not compete for binding. In some aspects, at least 3 cell types are tested. In some aspects, at least 10 chemokines are tested.

In some aspects, the chemokines are selected from the group consisting of CL1, XCL2, CX3CL1, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28. In some aspects, the chemokines are tethered to a solid support.

In some aspects, the testing step comprises determining the ability of the chemokines to compete with a ligand that binds to the chemokine receptor in each cell type. In some aspects, the ligand is labeled.

In some aspects, at least one cell type expresses an endogenous chemokine receptor. In some aspects, at least one cell type expresses a recombinantly expressed chemokine receptor. In some aspects, the cell types tested comprise a cancer cell and a non-cancer cell.

The invention also provides methods of detecting a first topology of a chemokine receptor in a sample. In some embodiments, the methods comprise: contacting the sample with an agent that binds to the first topology but not a second topology, and detecting whether the agent binds to the sample, thereby detecting the first topology of the chemokine receptor. In some embodiments, the agent is an antibody. In some embodiments, the sample is from a human. In some embodiments, agent binding indicates the presence or absence of a disease or condition related to a chemokine receptor. In some embodiments, the disease is selected from the group consisting of breast cancer, ovarian cancer, cervical cancer, Burkitt's lymphoma-associated cancer and glioblastoma-associated cancer. In some embodiments, the chemokine receptor is CXCR4. In some embodiments, the agent specifically binds CXCR4 when contacted to CXCR4 in a breast cancer cell, ovarian cancer cell, cervical cancer cell, Burkitt's lymphoma cell or glioblastoma cell, but does not bind CXCR4 when contacted to CXCR4 in a lymphocyte. In some embodiments, the breast cancer cell is MCF-7. In some embodiments, the chemokine receptor is CCR1. In some embodiments, the agent specifically binds CCR1 when contacted to CCR1 in an immature dendritic cell or neutrophil, but does not bind CCR1 when contacted to CCR1 expressed in a monocyte.

The invention also provides methods of treating a disease or condition related to a chemokine receptor in an animal, the method comprising administering a therapeutic dose of the agent identified as described above to an animal in need thereof. In some embodiments, the disease is selected from the group consisting of breast cancer, ovarian cancer, cervical cancer, Burkitt's lymphoma-associated cancer and glioblastoma-associated cancer. In some embodiments, the agent comprises an antibody. In some embodiments, the agent is an immunotoxin. In some embodiments, the animal is a human. In some embodiments, the disease is an inflammatory disorder.

The invention also provides methods of purifying cells that bind an agent specific for a first topology of a chemokine receptor, but not a second topology. In some embodiments, the methods comprise: contacting a sample comprising cells to an agent that binds to the first topology but not a second topology; and selecting cells that bind to the agent. In some embodiments, the agent is an antibody. In some embodiments, the agent is a ligand of the first topology but not the second topology. In some embodiments, the cell is a leukocyte.

The invention also provides methods of identifying an agent that modulates binding of a non-viral pathogen to a cell. In some embodiments, the methods comprise: (i) providing a first cell comprising a chemokine receptor having a first topology and a second cell comprising the chemokine receptor having a second topology; (ii) contacting an agent to the chemokine receptors; and (iii) selecting an agent that: (a) binds to the first topology of the chemokine receptor but not the second topology, and (b) modulates binding of a non-viral pathogen to a cell. In some embodiments, the pathogen is a parasite or a bacteria. In some embodiments, the first cell is infected with a non-viral pathogen. In some embodiments, the chemokine receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, CXR1, CCXCKR (CCR11), (CCR12), US28, ECRF3, Kaposi's Sarcoma-associated Herpesvirus GPCR, Poxvirus membrane-bound G Protein-coupled receptors, D6, and DARC.

The invention also provides antibodies that specifically binds CXCR4 in a MCF-7 cell, but does not bind CXCR4 in a lymphocyte.

The invention also provides antibodies that specifically binds to CCR1 in a neutrophil, but does not bind CCR1 in a monocyte.

The invention also provides methods of identifying a cancer cell in a biopsy. In some embodiments, methods comprise determining whether I-TAC binds to CXCR4 in a tissue sample, wherein binding of I-TAC to the CXCR4 indicates the presence of a cancer cell. In some embodiments, the methods comprise providing a tissue biopsy; and determining whether the tissue contains cells comprising a topology of CXCR4 that binds I-TAC, wherein the presence of a topology of CXCR4 that binds I-TAC indicates the presence of cancer cells. In some of these embodiments, I-TAC binding is determined by testing whether I-TAC competes with SDF-1 in a CXCR4 binding assay. In some embodiments, the cancer cell is selected from the group consisting of a breast cancer cell, an ovarian cancer cell, cervical cancer cell, a Burkitt's lymphoma cell and a glioblastoma cell.

The present invention also provides kits for detecting I-TAC binding to CXCR4. In some embodiments, the kits comprise chemokines I-TAC and SDF-1, wherein at least one of the chemokines is labeled; and a solid support or receptacle for measuring chemokine-CXCR4 binding. In some embodiments, the kits comprise an antibody that specifically binds to I-TAC. In some embodiments, the kits comprise salt buffers or other reagents for use in a chemokine competitive binding assay.

The present invention also provides methods of identifying an agent that modulates viral binding to a chemokine receptor having a first topology but not a second topology. In some embodiments, the methods comprise: (i) providing a first cell comprising a chemokine receptor in the first confirmation and a second cell comprising the chemokine receptor having a second topology; (ii) contacting an agent to the chemokine receptors; and (iii) selecting an agent that (a) binds to the first topology of the chemokine receptor but not the second topology, and (b) modulates viral binding to a chemokine receptor, thereby identifying an agent that modulates viral binding to a chemokine receptor having the first topology but not a second topology.

In some embodiments, the virus is selected from the group consisting of retroviruses and pox viruses. In some embodiments, the retrovirus is a lentivirus. In some embodiments, the lentivirus is a human immunodeficiency virus. In some embodiments, the pox virus is a leporipoxvirus. In some embodiments, the leporipoxvirus is a myxoma virus.

In some embodiments, the chemokine receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, CXR1, CCXCKR (CCR11), (CCR12), US28, ECRF3, Kaposi's Sarcoma-associated Herpesvirus GPCR, Poxvirus membrane-bound G Protein-coupled receptors, D6, and DARC. In some embodiments, the first cell is a leukocyte. In some embodiments, the leukocyte is a T-cell. In some embodiments, the agent competes with a virus for binding to the chemokine receptor.

The invention also provides methods of treating or preventing infection by a virus that binds to a chemokine receptor having a first topology but not a second topology. In some embodiments, the methods comprise administering a therapeutic dose of the agent identified as described above to an animal in need thereof. In some embodiments, the virus is selected from the group consisting of retroviruses and pox viruses. In some embodiments, the retrovirus is a lentivirus. In some embodiments, the lentivirus is a human immunodeficiency virus. In some embodiments, the pox virus is a leporipoxvirus. In some embodiments, the leporipoxvirus is a myxoma virus. In some embodiments, the animal is a human.

The present invention also provides a method of inducing apoptosis in a cancer cell. In some embodiments, the method comprises contacting the cancer cell with an SDF-1 antagonist. In some embodiments, the cancer cell is selected from the group consisting of a breast cancer cell, an ovarian cancer cell, cervical cancer cell, a Burkitt's lymphoma cell and a glioblastoma cell.

DEFINITIONS

"Antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to V$_H$-C$_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

"Cell or tissue responses" refers to a change of state of a cell or tissue and includes cellular responses induced by chemokine ligand binding to chemokine receptors. Defined responses which may be stimulated by chemokine receptors include transmembrane signaling, activation of cytoplasmic signaling cascades, cytoskeletal rearrangement, adhesion, chemotaxis, invasion, metastasis, cytokine production, gene induction, gene repression, induction of protein expression, or modulation of cellular growth and differentiation, including the development of cancer.

"Chemokine" or "chemokine ligand" refers to a small protein composed of approximately 50 to 110 amino acids and sharing sequence homology with other known chemokines (see, e.g., Murphy, P. M., *Pharmacol Rev.* 52:145-176 (2000)). Chemokines are classified according to the relative positions of the first pair of cysteines (Cs) found in the primary amino acid sequence. In CXCL chemokines, the first pair of cysteines is separated by any single amino acid. CCL chemokines have adjacent cysteines. In the CX3CL chemokines, the first cysteine pair is separated by 3 amino acids. CL chemokines contain only a single cysteine in the homologous position. Chemokines can trigger biological function by binding to and activating chemokine receptors.

A "chemokine receptor" refers to a polypeptide that specifically interacts with a chemokine molecule. A chemokine receptor is a G-protein coupled receptor with seven transmembrane domains. Chemokine receptors possess several common structural features including a highly acidic N-terminal domain; the amino acid sequence DRYLAIVHA (SEQ ID NO:4) (or a minor variation of that sequence) found within the second extracellular loop; a short third intracellular loop with an overall basic charge; a cysteine residue within each of the four extracellular domain. Typically, chemokine receptors have an overall size of approximately 340-370 amino acid residues. See, e.g., reviewed in Murphy, P. M. *Chemokine Receptors; Overview*, Academic Press 2000; and Loetscher P. and Clark-Lewis I. J. *Leukocyte Bid.* 69:881 (2001). Exemplary chemokine receptors include, e.g., CC-chemokine receptors (including CCR1, CCR2, CCR3, CCR4, CCR5, CCR6, CCR7, CCR8, CCR9, and CCR10), CXC-chemokine receptors (including CXCR1, CXCR2, CXCR3, CXCR4, CXCR5 and CXCR6), CX3CR1, CXR1, CCXCKR (CCR11), the virally-encoded chemokine receptors, US28, ECRF3, Kaposi's Sarcoma-associated Herpesvirus GPCR, Poxvirus membrane-bound G Protein-coupled receptors; D6, and DARC.

The terms "peptidomimetic" and "mimetic" refer to a synthetic chemical compound that has substantially the same structural and functional characteristics of antagonists or agonists of a chemokine receptor. Peptide analogs are commonly used in the pharmaceutical industry as non-peptide drugs with properties analogous to those of the template peptide. These types of non-peptide compound are termed "peptide mimetics" or "peptidomimetics" (Fauchere, J. *Adv. Drug Res.* 15:29 (1986); Veber and Freidinger *TINS* p. 392 (1985); and Evans et al. *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of, e.g., —CH2NH—, —CH2S—, —CH2-CH2-, —CH=CH— (cis and trans), —COCH2-, —CH(OH)CH2-, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of inhibiting or increasing the activity or function of a chemokine receptor.

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "ligand" refers to an agent, e.g., a polypeptide of other molecule capable of binding to a chemokine receptor.

As used herein, "an agent that binds to a topology of a chemokine" refers to an agent that binds with a high affinity. "High affinity" refers to an affinity sufficient to induce a pharmacologically relevant response, e.g., the ability to significantly compete for binding with a natural chemokine ligand to a chemokine receptor at pharmaceutically relevant concentrations (e.g., at concentrations lower than about $10^{-5}$ M.) See, e.g., Example 1 and FIG. 5. Some exemplary agents with high affinity will bind to a topology of a chemokine receptor with an affinity greater than $10^{-6}$ M, and sometimes greater than $10^{-7}$ M, or $10^{-8}$ M. An agent that fails to compete for binding with a natural receptor ligand when the agent is in a concentrations lower than $10^{-4}$ M will be considered to "not bind" for the purposes of the invention.

"Viral binding" refers to the ability of a virus particle or a portion of a virus, such as a viral envelope protein or fragment thereof, to bind to a target component such as a protein (e.g., a chemokine receptor). Binding can be measured using standard assays to determine binding affinity. Such assays include, e.g., competitive binding studies.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

"Topology" refers to a three-dimensional structure of a molecule, including but not limited to conformations. One polypeptide can form two or more topologies when the amino acid residues of the polypeptide form different structures. While a particular amino acid sequence can form two topologies, those of skill in the art will appreciate that the two topologies can sometimes also be represented by two different amino acid sequences, e.g., two sequences that vary by conservative changes. In addition, while topologies can be referred to as a "first" and a "second," this does not necessarily limit a polypeptide to only two topologies. The topology of a polypeptide can be altered by, e.g., sulfation, desulfation, myristylation, demyristylation, glycosylation, deglycosylation, phosphorylation or dephosphorylation. For example, chemokine receptor topology is determined, in some embodiments, by the cellular context in which the chemokine receptor is expressed. Cell-specific receptor topologies can arise as a result of interactions between chemokine receptors with each other (dimer or multimer formation) or with other cell surface proteins. In addition, a specific topology can be determined by other cell-specific components such as heterotrimeric G proteins, receptor interacting proteins, cellular signal transducing molecules, or the membrane phospholipid environment. Intracellular G protein subunits capable of modulating chemokine receptor topology could include, but are not limited to; G alpha, beta or gamma subunits. Receptor-interacting and modulating proteins also include, but are not limited to, RAMPs, cytoskeletal proteins, adaptor proteins, receptor kinases and other membrane associated enzymes.

The topology of a polypeptide can be determined by analyzing the binding affinities of antibodies or small molecules, such as antagonists or agonists, to a receptor topology as described herein. Specifically, different topologies can be identified by, e.g., 1) different antibody reactivity, including monoclonal antibody reactivity; 2) different ligand binding specificities, 3) different ligand affinities, 4) pharmacological discrimination (i.e., differential ability to bind to and/or be stimulated by small molecules), and 5) altered cellular responses, e.g., in response to ligand binding.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region or the entire sequence of a polynucleotide, e.g., encoding a chemokine receptor listed above such as CXCR4 (see, e.g., SEQ ID NO:1 and PCT WO 01/70768), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, flow cytometry and FACS analysis or immunohistochemistry are routinely used to select monoclonal antibodies specifically immunoreactive with a protein. See, e.g., Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

"Inhibitors," "activators," and "modulators" of chemokine receptor activity are used to refer to inhibitory, activating, or modulating molecules, respectively, identified using in vitro and in vivo assays for chemokine receptor binding or signaling, e.g., ligands, agonists, antagonists, and their homologs and mimetics. The term "modulator" includes inhibitors and activators. Inhibitors are agents that, e.g., bind to, partially or totally block stimulation, decrease, prevent, delay activation, inactivate, desensitize, or down regulate the activity of chemokine receptors, e.g., antagonists. Activators are agents that, e.g., bind to, stimulate, increase, open, activate, facilitate, enhance activation, sensitize or up regulate the activity of chemokine receptors, e.g., agonists. Modulators include agents that, e.g., alter the interaction of chemokine receptors with: proteins that bind activators or inhibitors, receptors, including G-proteins coupled-receptors (GPCRs), kinases, etc. Modulators include genetically modified versions of naturally-occurring chemokine receptor ligands, e.g., with altered activity, as well as naturally occurring and synthetic ligands, antagonists, agonists, small chemical molecules and the like. Such assays for inhibitors and activators include, e.g., applying putative modulator compounds to a cell expressing a chemokine receptor and then determining the functional effects on chemokine receptor signaling, as described above. Samples or assays comprising chemokine receptor that are treated with a potential activator, inhibitor, or modulator are compared to control samples without the inhibitor, activator, or modulator to examine the extent of inhibition. Control samples (untreated with inhibitors) are assigned a relative chemokine receptor activity value of 100%. Inhibition of chemokine receptor is achieved when the chemokine receptor activity value relative to the control is about 80%, optionally 50% or 25-0%. Activation of chemokine receptor is achieved when the chemokine receptor activity value relative to the control is 110%, optionally 150%, optionally 200-500%, or 1000-3000% higher.

BRIEF DESCRIPTION OF THE DRAWINGS

FIG. 6 illustrates reactivity of CCR1 specific antibodies to CCR1 on different cell types.

FIG. 7 illustrates $^{125}$I MIP-1α binding data.

FIG. 8 illustrates cell migration data for different cell/ligand combinations.

FIG. 9 illustrates intracellular Ca2+ mobilization.

FIG. 10 illustrates antibody reactivity data.

DETAILED DESCRIPTION OF THE INVENTION

1. Introduction

Figure 1:
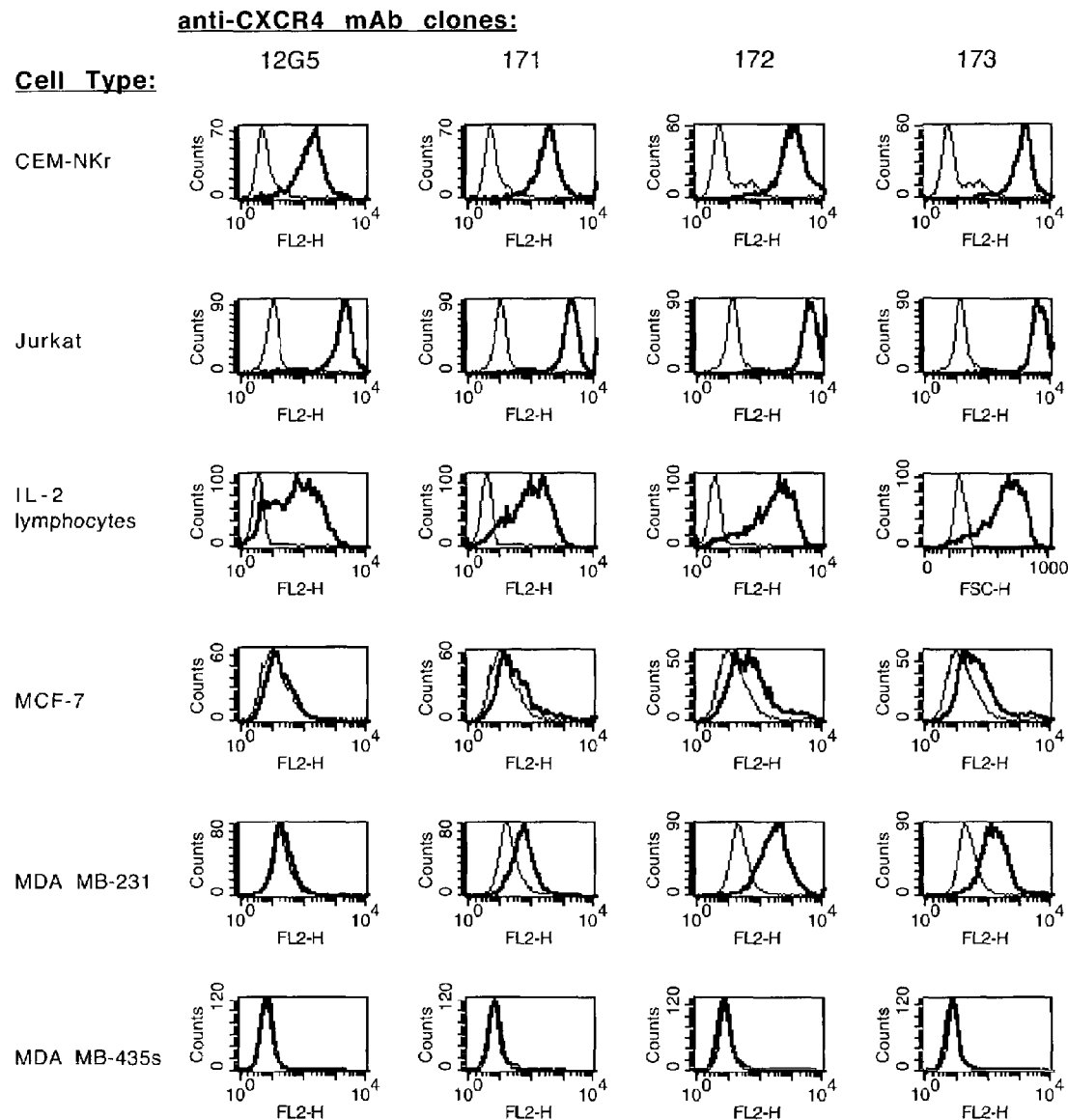
FIG. 1 illustrates antibody reactivity graphs. Antibody reactivity predicts and defines potential T cell vs. breast tumor cell receptor topology phenotype. The T cell lines, CEM-NKr and Jurkat, as well as normal PBMC were stained with the anti-CXCR4 antibody clones 12G5, 171, 172 and 173. Strong antibody reactivity is shown in comparison to the weak reactivity on the breast tumor lines, MCF-7, MDA MB-231 and MDA MB-435s. While MDA MB-435s exhibits no positive staining with any clone tested MCF-7 and MDA MB-231 demonstrate weak reactivity with clones 171, 172 and 173 but not 12G5. Thick black line, anti-CXCR4 antibody; thin black line, matched isotype control.

The present invention provides the surprising discovery that chemokine receptors form different topologies on different cell types. Different cell types have different ligand specificity, pharmacological features and function. A topology is a state or form of a protein (e.g., a chemokine receptor protein). Different topologies can be encoded by identical polynucleotides and can have similar or identical amino acid sequences. Different topologies of a chemokine receptor have distinct properties and may mediate different biological and/or pathological functions.

Differences between topologies can be ascertained, for example, by one or more of the following criteria:

1) Antibody reactivity—Different topologies encoded by a given receptor gene exhibit different staining profiles in response to a panel of antibodies (such as monoclonal antibodies raised against recombinant proteins representing the receptor polypeptide). Different topologies can occur when the identical chemokine receptor gene is expressed in different cell types.

2) Ligand binding—Different topologies encoded by a given receptor gene vary in their ligand binding profile (i.e., they bind to a different spectrum of discrete ligands). Furthermore, different topologies may bind ligands within their spectrum of ligands with different affinities.

3) Pharmacologic discrimination—Different topologies encoded by a given receptor gene are inhibited by discrete organic small molecules (or sets of small molecules), some of which may have medicinal relevance.

4) Function—Different topologies encoded by a given receptor gene control or impart different biological functions in different cellular or pathophysiological contexts. They differentially control a function (e.g., cell migration) by possessing different ligand binding spectrums in different cellular contexts. Different topologies differentially control cellular functions by differential coupling and second messenger signaling in different cellular contexts (such as by linking to different G proteins, etc.).

The present invention provides methods for identifying an agent that specifically binds and/or modulates one topology of a chemokine receptor but not a second topology of the receptor. Such agents are useful as therapeutics for diseases or conditions associated with a particular chemokine receptor topology. Moreover, the agents are useful for detecting a particular topology of a chemokine receptor, thereby diagnosing disease or predisposition for a disease. In addition, the agents are useful for identifying and isolating cells that express a particular topology of a chemokine receptor.

In some embodiments, the agents are useful to block viral binding to specific topologies of a chemokine receptor. Thus, the agents are useful for preventing or treating viral infections.

II. Identification of Topologies of a Chemokine Receptor

Novel topologies of a chemokine receptor can be identified by a number of methods. To identify cell-specific topologies, at least two cell types are provided and screened for differences in antigenicity, ligand binding or other ability associated with a chemokine receptor. Once a cell type expressing a suspected novel topology of a chemokine receptor is identified, the topology on the cell type can be further characterized as described herein (e.g., for antigenicity, ligand binding, small molecule affinity, function, etc.). As demonstrated in the examples, differential ligand specificity of the same or different receptor indicates that different cells support different topologies of the receptor.

The type of cells screened can vary greatly. In some embodiments, cell types known to express a particular chemokine receptor will be used. Exemplary chemokine receptors include, e.g., CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, CXR1, CCX-CKR (CCR11), (CCR12), US28, ECRF3, Kaposi's Sarcoma-associated Herpesvirus GPCR, Poxvirus membrane-bound G Protein-coupled receptors, D6, and DARC.

In other embodiments, it is not initially known whether a cell type expresses a particular receptor. In addition, cells representing different disease states (e.g., cancer cells) can be screened and compared. In some embodiments, the cells express an endogenous chemokine receptor. In other embodiments, at least some cell types express a recombinantly expressed chemokine receptor. Any number of cell types can be screened at one time. At least about 2, 3, 4, 5, 6, 7, 8, 9, 10, 15, 20, 50 or 100 or more different cell types can be screened at one time.

In some embodiments, the ligand binding properties of a chemokine receptor on the different cell types is compared. In such embodiments, the ligands can be any molecule that binds to at least one topology of a chemokine receptor. Exemplary ligands include naturally-occurring chemokines and other small molecules. Exemplary chemokines include, e.g., the following: XCL1, XCL2, CX3CL1, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28. See, e.g., Zlotnick et al., *Immunity* 12:121 (2000).

In some cases, a chemokine receptor having the first topology binds to a first and a second chemokine, the first and second chemokines compete for binding to the chemokine receptor having the first topology, and the chemokine receptor having the second topology binds to the first but not the second chemokine. In one example, the receptor having the first topology binds SDF-1 and I-TAC and the receptor having the second topology binds to SDF-1 but not I-TAC. Thus, an agent can be selected by identifying an agent that competes with SDF-1 and I-TAC for binding to the receptor having the first topology. The chemokine receptor having the first topology and the chemokine having the second topology can be identical, or can be, e.g., at least 99%, 95%, 90%, 80%, 70% 60% or 50% identical at the amino acid level.

The number of ligands screened on the different cell types can vary greatly. Typically the binding of at least 4, 5, 6, 8, 10, 15, 20, 30, 40, 50, 75, 100, or more ligands are compared.

One convenient method for screening the binding properties of a series of potential ligands involves measuring the ability of the potential ligands to compete for binding of a known ligand of the chemokine receptor of interest. See, e.g., Gosling et al., *J. Immunol.* 164:2851-2856 (2000); Dairaghi et al., *J. Biol. Chem.* 274(31):21569-21574 (1999). Competition assays are well known in the art. Typically, a known ligand is labeled so that differences in binding (e.g., in the presence of increasing amount of a potential competition ligand) can be measured. Competition assays indicate the affinity of potential competitor ligands. Statistically significant differences in affinity of a particular ligand for the same receptor expressed on different cell types indicates that different topologies are present on the different cell types.

In some embodiments of the methods, the potential ligands are tethered to a solid support. See, e.g., Gosling et al., supra.

III. Development of Specific Therapeutics Based upon Protein Topologies

Modulators of chemokine receptors, i.e. agonists or antagonists or agents of chemokine receptor activity, are useful for treating a number of mammalian diseases.

Diseases or conditions of humans or other species which can be treated with antagonists of a chemokine receptor or other inhibitors of chemokine receptor function, include, but are not limited to: acute or chronic inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers including breast cancer (e.g., mammary adenocarcinoma and mammary ductal carcinoma), glioblastomas, gliomas, lymphomas (e.g., Burkitt's lymphoma), melanomas, lung cancers, thyroid carcinomas, colon cancers, liver cancers, ovarian cancers, cervical cancers, pancreatic cancers, renal cell carcinomas, squamous cell carcinomas, brain tumors and skin cancer. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis, arteriosclerosis, autoimmune encephalomyelitis, ischemic reflux disorders, stroke, brain or spinal chord damage, and burns.

Diseases or conditions of humans or other species which can be treated with agonists of chemokine receptors or other promoters of chemokine receptor function, include, but are not limited to: immunosuppression, such as that in individuals with immunodeficiency syndromes, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (*Trichuriasis, Enterobiasis, Ascariasis,* Hookworm, *Strongyloidiasis, Trichinosis, filariasis*); trematodes (flukes) (*Schistosomiasis, Clonorchiasis*), cestodes (tape worms) (*Echinococcosis, Taeniasis saginata, Cysticercosis*); visceral worms, visceral larva migrans (e.g., *Toxocara*), eosinophilic gastroenteritis (e.g., *Anisaki* spp., *Phocanema* ssp.), and cutaneous larva migrans (*Ancylostona braziliense, Ancylostoma caninum*). Agonists of chemokine receptors or other promoters of chemokine receptor function are also useful in treating bacterial infections such as Pertussis (*Bordetella pertussis*); Cholera (*Vibrio cholerae*); Meningitis (*Neisseria meningitidis,*); Lyme Disease (*Borrelia burgdorferi,*); Haemophilus B (*Haemophilus influenza* B); Pneumonia (*Streptococcs pneumoniae*) Typhoid (*Salmonella typhi*), Diphtheria (*Corynebacterium diphtheriae*) and Tetanus (*Clostridium tetani*). Agonists of chemokine receptors or other promoters of chemokine receptor function are also useful in treating viral infections such as Influenza virus; Hepatitis A; Hepatitis B; Hepatitis C; Measles; Rubella virus; Mumps; Rabies; Poliovirus; Japanese Encephalitis virus; Rotavirus; Varicella.

The modulators of topologies of a chemokine receptor are accordingly useful in the prevention and treatment of a wide variety of inflammatory and immunoregulatory disorders and diseases.

Several different viruses are known to initiate cell infection by binding to chemokine receptors. For example, both retroviruses such as HIV ((see, e.g., Locati et al. *Annu. Rev. Med.* 50:425 (1999); Hurok *Immunol. Today* 20:89 (1999); Berson et al. *Semin. Immunol.* 10:237 (1998); and Littman et al., *Cell* 93:677 (1998)) and pox viruses such as myxoma virus (see, e.g., Lalani et al. *Science* 286:1968-1971 (1999)) bind to cells via chemokine receptors. The present invention provides for methods of identifying agents that prevent binding of these and other viruses to the particular topology of their chemokine receptors. These agents are useful as therapeutic compositions to prevent and treat viral diseases. For example, HIV strain R5 binds to chemokine receptor CCR5 while HIV strain X4 binds to CXCR4. Pox virus myxoma binds to receptors CCR1, CCR5 and CXCR4. These viruses can prevented from infecting cells by treating a patient with agents that bind to a particular topology of the chemokine receptor that the viruses bind to, thereby preventing infection. Other exemplary viruses that can be treated according to the methods of the invention, include, but are not limited to the Retroviridae, including Mammalian type B retroviruses such as mouse mammary tumor virus; Mammalian type C retroviruses such as murine leukemia virus; Avian type C retroviruses such as avian leukosis virus; Type D retroviruses such as Mason-Pfizer monkey virus; BLV-HTLV retroviruses such as bovine leukemia virus; Lentivirus such as human immunodeficiency virus 1; Spumavirus such as human spumavirus; as well as Pox viruses, including the Chordopoxvirinae, e.g., Orthopoxvirus such as vaccinia virus; Parapoxvirus such as orf virus; Avipoxvirus such as fowlpox virus; Capripoxvirus such as sheeppox virus; Leporipoxvirus such as myxoma virus; Suipoxvirus such as swinepox virus; Molluscipoxvirus such as Molluscum contagiosum virus; and Yatapox virus such as Yaba monkey tumor virus.

A. Methods of Identifying Modulators of Topologies of Chemokine Receptors

A number of different screening protocols can be utilized to identify agents that modulate the level of activity or function of a particular topology of a chemokine receptor in cells, particularly in mammalian cells, and especially in human cells. In general terms, the screening methods involve screening a plurality of agents to identify an agent that interacts with a specific a topology of a chemokine, for example, by binding to a chemokine receptor, preventing an inhibitor from binding to a chemokine receptor or activating a chemokine receptor. In some embodiments, the antagonist or agonist modulates the activity of only one topology of a chemokine receptor and not a second topology. In some embodiments, the antagonists or agonists modulate a chemokine receptor having a first topology but not a chemokine receptor having a second topology. In some embodiments, all chemokine receptor topologies are modulated by the antagonist or agonist. In some embodiments, an agent binds to one topology with at least about 1.5, 2, 3, 4, 5, 10, 20, 50, 100, 300, 500, or 1000 times the affinity of the agent for a second topology. In some embodiments, an agent binds to one topology with less than about 0.5, 0.3, 0.2, 0.1, 0.05, 0.01, 0.001 times the affinity of the agent for a second topology.

1. Chemokine Receptor Binding Assays

Preliminary screens can be conducted by screening for agents capable of binding to a topology of a chemokine receptor, as at least some of the agents so identified are likely chemokine receptor modulators. The binding assays usually involve contacting a topology of a chemokine receptor protein with one or more test agents and allowing sufficient time for the protein and test agents to form a binding complex. Any binding complexes formed can be detected using any of a number of established analytical techniques. Protein binding assays include, but are not limited to, immunohistochemical binding assays, flow cytometry or other assays which maintain the topology of a chemokine receptor. The chemokine receptor utilized in such assays can be naturally expressed, cloned or synthesized.

Binding assays are also useful, e.g., for identifying endogenous proteins that interact with a particular topology of a chemokine receptor. For example, antibodies, receptors or other molecules that bind the topology can be identified in binding assays.

2. Cells and Reagents

The screening methods of the invention can be performed as in vitro or cell-based assays. In vitro assays are performed when the chemokine receptor can form different topologies in solution. Cell based assays can be performed in any cells in which a chemokine receptor is expressed.

Cell-based assays involve whole cells or cell fractions containing a chemokine receptor to screen for agent binding or modulation of activity of the topology of the chemokine receptor by the agent. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells, endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, chemokine receptors can be expressed in cells that do not contain a particular endogenous chemokine receptor. In some embodiments, one topology of a chemokine receptor is expressed on one type of cell (e.g., a breast tumor cell, ovarian carcinoma, cervical carcinoma, Burkitt's lymphoma, glioblastoma, or a cell capable of supporting infection by a virus) while a second topology is expressed on a second cell type (e.g., a non-tumor cell or a cell not capable of supporting infection by a virus). A chemokine receptor does not necessarily only have two topologies. Thus an agent can be screened for the ability to interact selectively or modulate any one topology and not bind to or modulate one or more other topologies. Similarly, if a chemokine receptor forms more than two topologies, agents can be selected to bind or modulate a subset of topologies (e.g., two out of three topologies) while not binding or modulating all of the topologies of the chemokine receptor.

Any chemokine receptor can be used according to the methods of the invention. Exemplary chemokine receptors include, e.g., CC-chemokine receptors CCR1-10; CXC-chemokine receptors, CXCR1-6; CX3CR1; CXR1; CCX-CKR (CCR11); (CCR12), the virally encoded chemokine receptors, US28, ECRF3, Kaposi's Sarcoma-associated Herpesvirus GPCR, Poxvirus membrane-bound G Protein-coupled receptors; D6; and DARC. In some cases, a chemokine receptor having the first topology binds to a first and a second chemokine, the first and second chemokines compete for binding to the chemokine receptor having the first topology, and the chemokine receptor having the second topology binds to the first but not the second chemokine. In one example, the receptor having the first topology binds SDF-1 and I-TAC and the receptor having the second topology binds to SDF-1 but not I-TAC. Thus, an agent can be selected by identifying an agent that competes with SDF-1 and I-TAC for binding to the receptor having the first topology. The chemokine receptor having the first topology and the chemokine having the second topology can be identical, or can be, e.g., at least 99%, 95%, 90%, 80%, 70% 60% or 50% identical at the amino acid level.

As discussed above, agents can be selected to bind or modulate a subset of topologies while not binding or modulating all of the topologies of the chemokine receptor. For example, agents can be screened for the ability to bind to or modulate a first topology of a chemokine receptor but not bind to or modulate the topology of a second topology of a second cell. In some embodiments, the first cell is a tumor cell while the second cell is a non-tumor cell or a different type of tumor cell. Exemplary tumor cells include, e.g., breast cancer cells, ovarian cancer cells, cervical carcinomas, glioblastomas, colon cancer cells, pancreatic cancer cells, prostate cancer cells, liver cancer cells, skin cancer cells, brain cancer cells, bone cancer cells, lung cancer cells, testicular cancer cells, Burkitt's lymphoma cells, and leukemia cells. Breast cancer cells include, e.g., MDA MB-231, MCF-7, ZR 75-1 and DU-4475. Chemokine receptors (e.g., CXCR4) can regulate the growth rate of tumor cells by mediating proliferative or antiproliferative intracellular signals. In some embodiments, a specific topology (or subset of topologies) can stimulate cancer cell proliferation. Agents that selectively modulate one topology (or topologies) of a chemokine receptor, but not another, therefore find utility as selective anti-cancer therapeutics.

Other exemplary cells that can be used to screen for modulators of one topology but not a second topology include, e.g., monocytes, neutrophils, immature dendritic cells and other immunological cells such T cells and B cells. As one alternative, two of the above listed cells types are used and molecules that bind to a receptor on one cell but not the second cell type are selected.

3. Signaling Activity

Signaling activity of a topology of a chemokine receptor can be determined in many ways. For example, signaling can be measured by determining, qualitatively and quantitatively, whether a modulator can induce calcium mobilization in a cell. Calcium mobilization assays are described in, e.g, Dairaghi et al., *J. Biol. Chem.* 272 (45): 28206-9 (1997). Other secondary messengers, such as cyclic AMP or inositol phosphates, as well as phosphorylation or dephosphorylation events can also be monitored. See, e.g., Premack, et al. *Nature Medicine* 2: 1174-1178 (1996) and Bokoch, *Blood* 86:1649-1660 (1995).

In addition, down stream molecular events can also be monitored to determine signaling activity. Downstream events include those activities or manifestations that occur as a result of stimulation of a chemokine receptor. Exemplary downstream events include, e.g., cell or tissue responses such as the development of lymphoid tissues (e.g., CXCR5), heart (e.g., CXCR4) or other tissues, changed state of a cell (e.g., from normal to cancer cell or primary cancer cell to metastatic cancer cell) as well as infection by a non-viral pathogen such as a bacteria, protozoa or other parasite. Tissue responses as used herein also encompass the development of inflammation in a tissue. Cell responses include chemotactic movement of cells (e.g., leukocytes) to attractants (e.g., chemokines) and cell invasion (e.g., tumor cells with invasive properties) to attractants (e.g., chemokines). Chemokine receptors have also been found to have a role in platelet activation and aggregation (see, e.g., Abi-Younes S. et al, *Circ Res.,* 86:131-138 (1999); Kowalska, M. A., et al, *Blood* 96:50-57(2000); and Clementson, K. J., et al, *Blood,* 96:4046-4054 (2000)) as well as the induction of apoptosis (see, e.g., Berndt C. et al., *Proc. Natl. Acad. Sci. USA,* 95:12556-12561 (1998).

4. Validation

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a model for humans and then determining if the chemokine receptor is in fact modulated and/or the disease or condition is ameliorated. The animal models utilized in validation studies generally are mammals of any kind. Specific examples of suitable animals include, but are not limited to, primates, mice and rats.

B. Agents Which Interact with Specific of Chemokine Receptors

The agents tested as modulators of at least one topology of a chemokine receptor can be any small chemical compound, or a biological entity, such as a polypeptide, sugar, nucleic acid or lipid. Alternatively, modulators can be genetically altered versions of a chemokine or other ligand. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, the agents have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5 H-bond donors (expressed as the sum of OHs and NHs); having a molecular weight over 500; having a LogP over 5 (or MLogP over 4.15); and/or having more than 10 H-bond acceptors (expressed as the sum of Ns and Os). See, e.g., Lipinski et al. *Adv Drug Delivery Res* 23:3-25 (1997). Compound classes that are substrates for biological transporters are typically exceptions to the rule.

CCX7923 (see, FIG. 5) is commercially available and can be made by the condensation of N-[3-(dimethylamino)propyl]-N,N-dimethyl-1,3-propanediamine with bromomethyl-bicyclo(2,2,1)hept-2-ene by methods known in the art. CCX0803 (see, FIG. 5) is commercially available and can be made by condensation of 3-(2-bromoethyl)-5-phenyl-methoxy-indole and 2,4,6-triphenylpyridine by methods well known in the art. See, e.g., *Organic Function Group Preparations,* 2nd Ed. Vol. 1, (S. R. Sandler & W. Karo 1983); *Handbook of Heterocyclic Chemistry* (A. R. Katritzky, 1985); *Encyclopedia of Chemical Technology,* 4th Ed. (J. I. Kroschwitz, 1996).

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, Jan. 18, 1993 page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

C. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule that binds the tag (a tag binder) is fixed to a solid support, and the tagged molecule of interest (e.g., a chemokine receptor) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:3). Such flexible linkers are known to those of skill in the art. For example, poly(ethelyne glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank and Doring, *Tetrahedron* 44:60316040 (1988) (describing synthesis of various peptide sequences on cellulose disks); Fodor et al., *Science*, 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the function or activity of a particular topology of a chemokine receptor. Control reactions that measure chemokine receptor activity of the cell in a reaction that does not include a potential modulator are optional, as the assays are highly uniform. Such optional control reactions are appropriate and increase the reliability of the assay. Accordingly, in a preferred embodiment, the methods of the invention include such a control reaction. For each of the assay formats described, "no modulator" control reactions which do not include a modulator provide a background level of binding activity.

In some assays it will be desirable to have positive controls to ensure that the components of the assays are working properly. At least two types of positive controls are appropriate. First, a known activator or ligand of the topology of interest of the chemokine receptor can be incubated with one sample of the assay, and the resulting increase in signal resulting from an increased activity of chemokine receptor determined according to the methods herein. Second, a known inhibitor or antagonist of a topology of the chemokine receptor can be added, and the resulting decrease in signal for the activity of the chemokine receptor can be similarly detected. It will be appreciated that modulators can also be combined with activators or inhibitors to find modulators which inhibit the increase or decrease that is otherwise caused by the presence of the known modulator of the chemokine receptor.

D. Computer-Based Assays

Yet another assay for compounds that modulate the activity or function of chemokine receptors involves computer assisted drug design, in which a computer system is used to generate a three-dimensional structure of a chemokine receptor based on the structural information encoded by its amino acid sequence. The input amino acid sequence interacts directly and actively with a pre-established algorithm in a computer program to yield secondary, tertiary, and quaternary structural models of the protein. Similar analyses can be performed on potential or known binding partners or ligands of chemokine receptors, including binding partners or ligands that only one topology of a chemokine receptor. The models of the protein structure are then examined to identify regions of the structure that have the ability to bind, e.g., a chemokine receptor. These regions are then used to identify polypeptides that bind to the chemokine receptor.

The three-dimensional structural model of the protein is generated by entering protein amino acid sequences of at least 10 amino acid residues or corresponding nucleic acid sequences encoding a potential chemokine receptor ligand into the computer system. The amino acid sequences encoded by the nucleic acid sequences provided herein represent the primary sequences or subsequences of the proteins, which encode the structural information of the proteins. At least 10 residues of an amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the chemokine receptor to identify binding sites of the chemokine receptor. Binding affinity between the protein and ligands is determined using energy terms to determine which ligands have an enhanced probability of binding to the protein.

IV. Detection of Different Topologies of Chemokine Receptors

Assays can be used to detect different topologies of a chemokine receptor of interest. For example, immunoassays can be used to qualitatively or quantitatively analyze the topology of a chemokine receptor. A general overview of the applicable technology can be found in Harlow & Lane, *Antibodies: A Laboratory Manual* (1988). Alternatively, non-antibody molecules with affinity for a particular topology of a chemokine receptor can also be used to detect the topology of a chemokine receptor.

Figure 2:
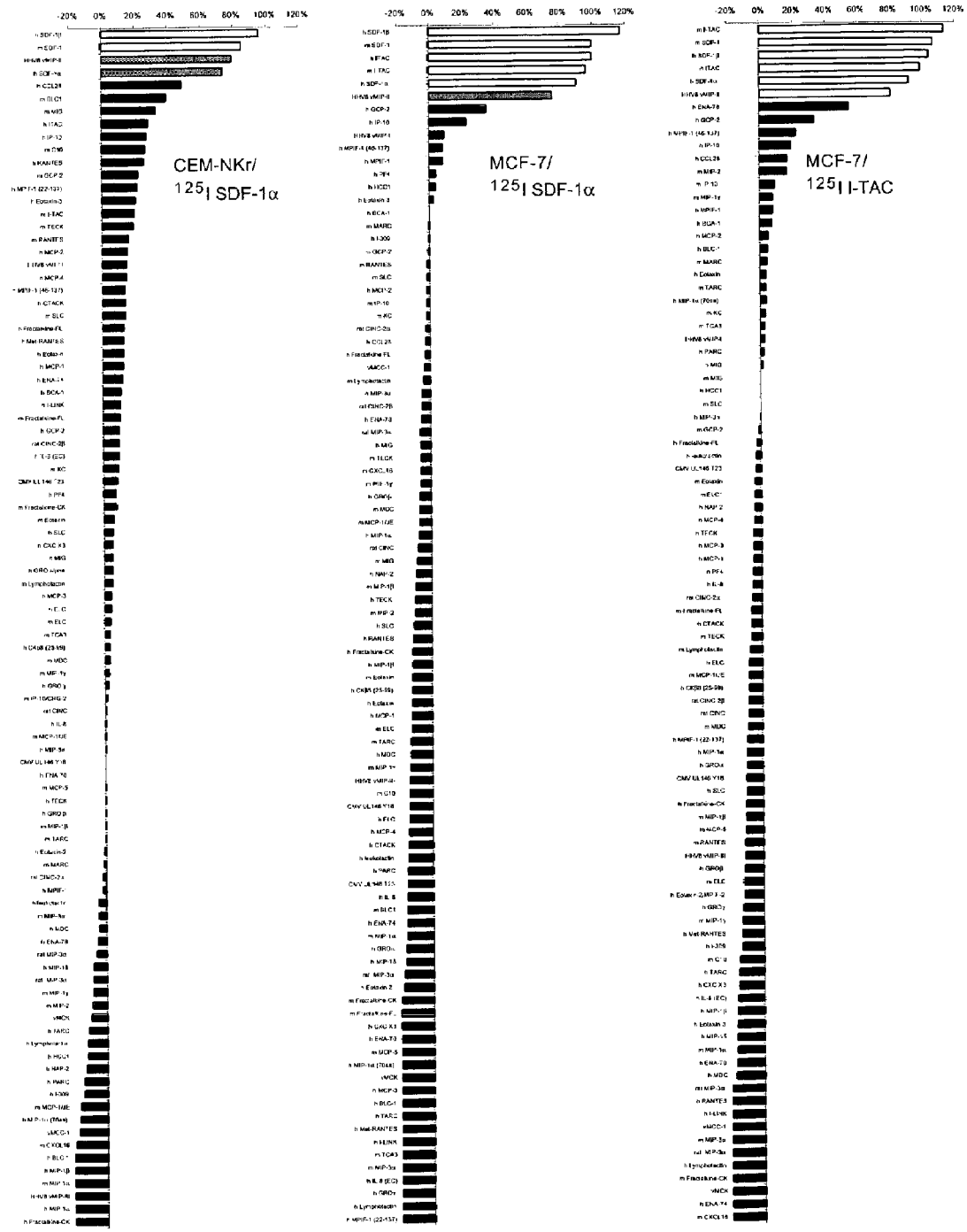
FIG. 2 illustrates binding data demonstrating a distinct SDF-1 displacement binding 'fingerprint' on different cell types. Binding competition profile using 125I SDF-1α as the radioligand probe on (a) CEM-NKr and (b) MCF-7, as well as $^{125}$II-TAC used as the radioligand probe on (c) MCF-7, in a binding displacement experiment with a comprehensive array of >90 discrete viral, human and murine chemokines and chemokine variants as cold competitors. The percent inhibition of radioligand binding is shown as a bar graph and reveals that SDF-1α and I-TAC are cross-displaced on MCF-7 but not CEM-NKr cells. White bars, potential high affinity (inhibition >80%); gray bars, potential moderate to low affinity (inhibition between 60-79%); black bars, little or no affinity (inhibition <60%). Results are the mean of three determinations. Error bars are omitted for clarity.

Ligand specificity can differ between topologies. Therefore, the ability to bind to a particular ligand (e.g., a chemokine) indicates the presence of a specific topology of a chemokine receptor. For example, as illustrated in FIG. 2, the ability of SDF-1α and I-TAC to compete for binding to the same chemokine receptor indicates that a novel topology is found in breast cancer cells. This method is similarly applicable for identifying other cancers (e.g., ovarian cancer, cervical cancer, gliomablastoma, Burkitt's lymphoma, etc.)

A. Antibodies to Target Proteins

Methods for producing polyclonal and monoclonal antibodies that react specifically with a protein of interest or specific topology of a protein are known to those of skill in the art (see, e.g., Coligan, supra; and Harlow and Lane, supra; Stites et al., supra and references cited therein; Goding, supra; and Kohler and Milstein *Nature,* 256:495-497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant protein is produced in a transformed cell line. An inbred strain of mice, rats, guinea pigs or rabbits is immunized with the protein using a standard adjuvant, such as Freund's adjuvant, and a standard immunization protocol. Alternatively, a synthetic peptide derived from the sequences disclosed herein and conjugated to a carrier protein can be used as an immunogen. A further option is to use a cell expressing the protein (e.g., in a particular topology) or a membrane fraction or liposome comprising a particular topology as an antigen. For example a breast cancer cell line expressing a breast cancer specific topology of CXCR4 can be used to raise antibodies specific for that topology. Antibodies raised against the cell, membrane fraction or liposome can then be selected for their ability to bind to the protein. This method is particularly useful if the particular topology of a protein is dependent on its expression in a particular cell type.

Polyclonal sera are collected and titered against the immunogen in an immunoassay, for example, a solid phase immunoassay with the immunogen immobilized on a solid support. Polyclonal antisera with a titer of $10^4$ or greater are selected and tested for their crossreactivity against a different topology of the chemokine receptor or even other homologous proteins, using a competitive binding immunoassay. Specific monoclonal and polyclonal antibodies and antisera will usually bind with a $K_D$ of at least about 0.1 mM, more usually at least about 1 μM, preferably at least about 0.1 μM or better, and most preferably, 0.01 μM or better.

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A number of proteins of the invention comprising immunogens may be used to produce antibodies specifically or selectively reactive with the proteins of interest. Recombinant protein is the preferred immunogen for the production of monoclonal or polyclonal antibodies. Naturally occurring protein may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to a particular topology of a chemokine receptor. When appropriately high titers of antibody to the immunogen are obtained, blood is collected from the animal and antisera are prepared. Further fractionation of the antisera to enrich for antibodies reactive to the protein can be done if desired (see, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., supra.

Once target protein-specific antibodies are available, the protein can be measured by a variety of immunoassay methods with qualitative and quantitative results. For a review of immunological and immunoassay procedures in general see, Stites, supra. Moreover, the immunoassays of the present invention can be performed in any of several configurations, which are reviewed extensively in Maggio *Enzyme Immunoassay*, CRC Press, Boca Raton, Fla. (1980); Tijssen, supra; and Harlow and Lane, supra.

Immunoassays to measure target proteins in a human sample may use a polyclonal antiserum which was raised to the protein (e.g., one topology of a chemokine receptor) or a fragment thereof. This antiserum is selected to have low cross-reactivity against other topologies of the chemokine receptor and any such cross-reactivity is removed by immunoabsorption prior to use in the immunoassay. Alternatively, antibodies that recognize more than one or even all chemokine receptor topologies in a sample can be used, for example to determine the overall level of chemokine receptor in a sample.

B. Immunological Binding Assays

In a preferred embodiment, a protein of interest is detected and/or quantified using any of a number of well-known immunological binding assays (see, e.g., U.S. Pat. Nos. 4,366,241; 4,376,110; 4,517,288; and 4,837,168). For a review of the general immunoassays, see also Asai *Methods in Cell Biology Volume 37: Antibodies in Cell Biology*, Academic Press, Inc. NY (1993); Stites, supra. Immunological binding assays (or immunoassays) typically utilize a "capture agent" to specifically bind to and often immobilize the analyte (in this case a topology of a chemokine receptor or antigenic subsequences thereof). The capture agent is a moiety that specifically binds to the analyte. In a preferred embodiment, the capture agent is an antibody that specifically binds, for example, a topology of a chemokine receptor. The antibody (e.g., anti-chemokine receptor antibody) may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111:1401-1406 (1973); and Akerstrom, et al. *J. Immunol.*, 135:2589-2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting proteins of interest from tissue samples may be either competitive or noncompetitive. Noncompetitive immunoassays are assays in which the amount of captured analyte (e.g., the protein) is directly measured. In one preferred "sandwich" assay, for example, the capture agent (e.g., anti-chemokine receptor antibodies) can be bound directly to a solid substrate where it is immobilized. These immobilized antibodies then capture the chemokine receptors in one topology present in the test sample. The chemokine receptor thus immobilized is then bound by a labeling agent, such as a second anti-chemokine receptor antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats

In competitive assays, the amount of target protein (analyte) present in the sample is measured indirectly by measuring the amount of an added (exogenous) analyte (i.e., a topology of interest of a chemokine receptor) displaced (or competed away) from a capture agent (i.e., an anti-chemokine receptor antibody) by the analyte present in the sample. In one competitive assay, a known amount of the protein of interest is added to the sample and the sample is then contacted with a capture agent, in this case an antibody that specifically binds to one topology of a chemokine receptor. The amount of immunogen bound to the antibody is inversely proportional to the concentration of immunogen present in the sample. In a particularly preferred embodiment, the antibody is immobilized on a solid substrate. For example, the amount of the chemokine receptor bound to the antibody may be determined either by measuring the amount of subject protein present in a chemokine receptor protein/antibody complex or, alternatively, by measuring the amount of remaining uncomplexed protein. The amount of chemokine receptor may be detected by providing a labeled chemokine receptor molecule.

Immunoassays in the competitive binding format can be used for cross-reactivity determinations. For example, the protein encoded by the sequences described herein can be immobilized on a solid support or on intact cells or natural or artificial membranes containing the protein of interest. Proteins (e.g., a second conformation of the chemokine receptor) are added to the assay that compete with the binding of the antisera to the immobilized antigen. The ability of the above proteins to compete with the binding of the antisera to the immobilized protein is compared to that of the protein encoded by any of the sequences described herein. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

3. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

V. Methods of Isolating Cells with a Binding Agent

Agents that specifically bind to a particular topology of a chemokine receptor can be used to isolate, identify and detect cell populations that carry that particular topology. For example, leukocyte subpopulations or tumor cells that express a particular topology can be detected in a sample. Alternatively, cells that express the particular topology can be isolated from a sample using the agent to bind to and purify cells expressing the topology from the sample. Exemplary methods of isolating cells include affinity chromatography and the use of cell cytometry and fluorescence activated cell sorter (FACS).

In addition, detection and isolation of cells displaying a particular topology can be achieved by using topology-specific chemokine ligands which are labeled (by fluorescence tags, radioactivity or other standard protein labeling methods) and used in cell sorting. Alternatively, the chemokine ligands may be attached to solid-phase (glass, plastic, latex bead, or magnetic bead) substrates as 'capture' agents. Such solid-phase capture methods are widely known as 'panning' technologies and can be used to isolate, purify and further concentrate cells expressing a specific topological form of a chemokine receptor of interest in diseased or normal cells.

VI. Compositions, Kits, Integrated Systems and Proteomic Applications

The invention provides compositions, kits and integrated systems for practicing the assays described herein using anti-chemokine receptor antibodies or other agents that specifically detect particular topologies of the receptors.

The invention provides assay compositions for use in solid phase assays; such compositions can include, for example, a specific topology of a chemokine receptor (e.g., as part of a cell, membrane fractions or liposomes (see, e.g., Babcok et al., *J. Biol. Chem.* 276(42):38433-40 (2001); Mirzabekov et al., *Nat. Biotechnol.* 18(6):649-54 (2000)) that maintain a topology) immobilized on a solid support, and a labeling reagent. In each case, the assay compositions can also include additional reagents that are desirable for hybridization. For example, the solid support can be, e.g., a petri plate, multi-well plate or microarray. In addition, microarrays of peptide libraries can be used to identify peptide sequences that specifically bind a particular topology of a chemokine receptor.

Agents that specifically bind to a topology of a chemokine receptor can also be included in the assay compositions. For example, an antibody that specifically binds to a particular topology of a chemokine receptor can be immobilized on a solid support. In some of these embodiments, the agent is used to detect for the presence or absence of a particular chemokine receptor topology or cells expressing that topology. For example, the solid support can be petri plate, multi-well plate or microarray.

The invention also provides kits for carrying out the assays of the invention. The kits typically include an agent (e.g., an antibody or other small molecule) that specifically binds to one topology of a chemokine receptor and a label for detecting the presence of the agent. The kits may include one or more chemokine receptor polypeptides. Kits can include any of the compositions noted above, and optionally further include additional components such as instructions to practice a high-throughput method of assaying for an effect on activity or function of chemokine receptors, one or more containers or compartments (e.g., to hold the probe, labels, or the like), a control modulator of the function or activity of chemokine receptors, a robotic armature for mixing kit components or the like.

In some cases, the kits comprise a chemokine receptor on which SDF-1α and I-TAC compete for binding. In some embodiments, the kits comprise components for detecting whether CXCR4 in a tissue sample binds to I-TAC. In some embodiments, the kits comprise, e.g., a labeled or tagged SDF-1 and cold competitor I-TAC or alternatively, a labeled or tagged I-TAC and cold competitor SDF-1. The labeled or tagged chemokine can be labeled or tagged in any way known to those of skill in the art. In some embodiments, the labeled chemokine is radiolabeled or tagged with biotin or a fluorescent label. Alternatively, or in addition, the kit can contain an anti-I-TAC binding reagent (e.g., an antibody) for detection of I-TAC. The kits can also contain the appropriate salt buffers and other reagents to perform a competitive binding assay, e.g., on intact cells or cell membranes. Such reagents are described in, e.g., the examples below. In some aspects, the kits also comprise a solid support or receptacle for measuring chemokine-CXCR4 binding (e.g., a plate format for reactions compatible with scintillation counters or automated plate readers). In some aspects, the kits comprise instructions for using the kits, e.g., in the methods of the invention.

The invention also provides integrated systems for high-throughput screening of potential modulators for an effect on the activity or function of the chemokine receptors. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS®, OS2® WINDOWS®, WINDOWS NT®, WINDOWS95®, WINDOWS98®, or WINDOWS2000® based computers), MACINTOSH®, or UNIX® based (e.g., SUN® work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

VII. Administration and Pharmaceutical Compositions

Modulators of a particular topology of a chemokine receptor (e.g., antagonists or agonists) can be administered directly to the mammalian subject for modulation of chemokine receptor signaling in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The modulators (e.g., agonists or antagonists) of the expression or activity of the chemokine receptors, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose scaled containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to effect a beneficial response in the subject over time. The optimal dose level for any patient will depend on a variety of factors including the efficacy of the specific modulator employed, the age, body weight, physical activity, and diet of the patient, on a possible combination with other drugs, and on the severity of a particular disease. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, chemokine receptor modulators of the present invention can be administered at a rate determined by the LD-50 of the modulator, and the side-effects of the modulator at various concentrations, as applied to the mass and overall health of the subject. Administration can be accomplished via single or divided doses.

VIII. Detection of Specific Topologies and Diagnosis of Disease

The present invention provides for methods of detecting a specific topology of a chemokine receptor in a sample. Detection methods using agents that bind a protein are well known and include, e.g., flow cytometry. Using flow cytometry, cells expressing a specific antigen of interest within a mixed population of cells can be identified. Briefly, cells are permitted to react with an antibody specific for the protein of interest (e.g., in one topology but not a second topology). The antibody can either be fluorescently labeled (direct method of staining), or if it is not labeled, a second antibody that reacts with the first can be fluorescently tagged (indirect method of staining). Cells are then passed through an instrument that can detect the fluorescent signal. Cells are aspirated and made into a single cell suspension. This cell suspension is passed by a laser that excites the fluorochrome labeled antibody now binding to the cells and acquires this data. Cells that are found to be bright (i.e. react with the fluorescently labeled antibody) express the protein of interest; cells that are dull (i.e. do not react with the fluorescently labeled antibody) do not express the protein of interest.

The present invention provides for methods of diagnosing which topology of a given chemokine receptor is involved in causing human diseases including, but not limited to cancer, including, e.g., breast cancer, ovarian cancer, cervical cancer, glioblastoma, leukemia and Burkitt's lymphomas, as well as rheumatoid arthritis, multiple sclerosis, cardiac allograft rejection, atherosclerosis, asthma, glomerulonephritis, contact dermatitis, inflammatory bowel disease, colitis, psoriasis, reperfusion injury, as well as other disorders and diseases described herein. For each of these diseases, the diagnosis may include evaluation of the specific topology of the chemokine receptor(s) involved, as characterized by a panel of selective monoclonal antibodies using flow cytometry or other methods of detecting molecules containing specific epitopes. As provided herein, including in the examples, normal and diseased cells and tissues can be distinguished based on different patterns of reactivity to a panel of defined anti-chemokine receptor monoclonal antibodies or chemokines. For example, cancer cells are detected by detecting on a cell a chemokine receptor for which SDF-1α and I-TAC compete for binding. In some embodiments, cancer cells can be detected in a sample by specifically detecting the CXCR4 topology found in MCF-7 cells.

In addition, differences in ligand binding between chemokine receptor topologies can be detected and such differences can be used to detect cells expressing a specific topology. Ligands can include naturally-occurring chemokines as well as small molecules with specificity for a particular topology. Where a disease state is associated with a specific cell type, detection of the cell type results in detection of the disease state. For example, as described herein, breast cancer cells express a chemokine receptor for which SDF-1α and I-TAC compete for binding.

In some cases, the topology of CXCR4 expressed on breast cancer cells specifically binds to the chemokine I-TAC. The topology of CXCR4 in IL-2 cultured lymphocytes and T cell lines do not bind to I-TAC. Therefore, the ability of cells to bind I-TAC via CXCR4 indicates the presence of cancer cells. In an exemplary method, a tissue biopsy is provided and it is determined whether the tissue contains cells comprising a topology of CXCR4 that binds I-TAC. The presence of a topology of CXCR4 that binds I-TAC indicates the presence of cancer cells. Detection of cancer cells by detecting I-TAC is useful, e.g., for diagnosis as well as in evaluating tissue either pre- or post-therapies (including chemotherapy) after diagnosis of cancer. The cancer cells can include, e.g., breast cancer cells, ovarian carcinomas, cervical carcinomas, Burkitt's lymphomas, glioblastomas, etc.

Specific binding of a chemokine to a particular chemokine receptor can be detected according to any method known to those of skill in the art. In an exemplary method, chemokine binding is detected in a competition experiment with a known chemokine receptor ligand. For example, to determine whether I-TAC binding is due to an interaction with CXCR4, it can be determined whether I-TAC binding can be competed with a known CXCR4 ligand such as SDF-1.

Chemokine binding can be determined using tissue samples (e.g., biopsies) or can be monitored directly in a tissue if situ (e.g., using radiolabelled chemokine imaging).

Once the chemokine receptor topology associated with a disease state is characterized using tissue samples, the chemokine receptor topology can be determined in diagnostic samples from patients. Such differences in chemokine receptor topology may then be utilized as a distinguishing characteristic or marker in the clinical diagnosis of that disease. The differential diagnosis of disease and current clinical status through chemokine receptor topology characterization provides a novel detection method that is correlative or predictive of the outcome or prognosis for chemokine receptor-mediated diseases.

IX. Vaccines

Chemokine receptor topologies are distinguished, inter alia, in terms of antibody-binding phenotypes. Antibody-binding phenotypes indicate that there are shared and unique epitopes on topologies of the same receptor while other epitopes are unique to a particular topology. Since different topologies of the same chemokine receptor have identical amino acid sequences, unique epitopes are created to distinguish different topologies. Unique epitopes of a particular topology are exploited for clinical use in cases where the unique epitope is expressed on pathology-inducing cells, e.g. tumor cells. In these cases, the shared epitopes of an individual receptor topology are identified by standard epitope mapping, e.g. by producing contiguous peptides (e.g., about 12-mer to about 18-mer) spanning the entire extracellular domain on the receptor, and evaluating binding of appropriate "shared" antibodies to those peptides. Fine detail epitope mapping on an individual antibody-binding peptide can be achieved by producing a family of related peptides varying one amino acid position each time. Once shared epitopes were identified, a recombinant form of the receptor is engineered to eliminate those shared epitopes. This can be achieved, e.g., by point mutagenesis of the cDNA encoding same receptor at the site of the shared epitope or other methods of mutating or altering the receptor. The mutated cDNA, or encoded polypeptide, which only contains the unique epitopes of one topology (e.g., a pathology-associated topology), is then utilized as an immunogen to prophylactically or therapeutically vaccinate individuals against the receptor topology expressed on pathology-causing cells, e.g. tumor cells. For example, in some embodiments, antigens containing unique epitopes of the CXCR4 topology found in MCF-7 cells are used to induce an immune response against cancer cells, e.g., breast cancer cells, cervical carcinomas, cervical carcinomas, Burkitt's lymphomas, glioblastomas or other cancer cells. In some embodiments, the mutated or altered cDNA is expressed in a suitable cell type, e.g. an HLA-matched cell type, by transfection into that cell. Cells expressing the mutated cDNA could be administered in a variety of ways, including by injection (e.g., intradermal, subcutaneous, intramuscular, intraperitonel, and the like). Alternatively, peptides containing unique epitopes but lacking shared epitopes could be conjugated to carriers and used as vaccines. In addition, the polynucleotides encoding epitopes specific for a particular topology of a chemokine receptor can be inserted into vectors and used for gene therapy.

Immunogens may be combined or mixed with various solutions and other compounds as are known in the art. Vaccines may be prepared as injectables, as liquid solutions or emulsions. The polypeptides of the invention may be mixed with pharmaceutically-acceptable excipients which are compatible with the polypeptides. Excipients may include water, saline, dextrose, glycerol, ethanol, and combinations thereof. The vaccine may further contain auxiliary substances such as wetting or emulsifying agents, pH buffering agents, or adjuvants to enhance the effectiveness of the vaccines.

Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionobacterium acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

The proportion of immunogen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the immunogen can range from about 5 μg to about 100 μg protein per patient. A preferable range is from about 20 μg to about 40 μg per dose.

A suitable dose size is about 0.5 ml. Accordingly, a dose for intramuscular injection, for example, would comprise 0.5 ml containing 20 μg of immunogen in admixture with 0.5% aluminum hydroxide.

Typically, the vaccines are formulated to contain a final concentration of immunogen in the range of from 0.2 to 200 μg/ml. After formulation, the vaccine may be incorporated into a sterile container that is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. The treatment may consist of a single dose of vaccine or a plurality of doses over a period of time. The immunogen of the invention can be combined with appropriate doses of compounds including other epitopes of the target cell. Also, the immunogen could be a component of a recombinant vaccine that could be adaptable for oral administration.

Regardless of whether one uses the intact receptor protein or fragments, there are conventional protocols for immunizing an animal such as a human. For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

Oral formulations may include normally employed excipients such as, for example, pharmaceutical grades of saccharine, cellulose and magnesium carbonate. These compositions take the form of solutions, suspensions, tablets, pills, capsules, sustained release formulations or powders and contain 10-95% of the polypeptides of the invention.

The peptides of this invention can be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. Various ways of such administration are known in the art. The pharmaceutical formulation for nasal administration may be prepared as solutions in saline, employing benzyl alcohol or other suitable preservatives, absorption promoters to enhance bioavailability, fluorocarbons, and/or other solubilizing or dispersing agents known in the art. The unit dosage for nasal administration can be from 7 to 3000 mg, preferably 70 to mg, and most preferably, 1 to 10 mg of active ingredient per unit dosage form.

EXAMPLES

Example 1

This example shows that CXCR4 forms different topologies in different cells.

Materials and Methods

Reagents and Cells. Human, viral and murine recombinant chemokines were obtained from R&D Systems (Minneapolis, Minn.) and PeproTech (Rocky Hill, N.J.) where indicated. $^{125}$I-labeled SDF-1a was purchased from PerkinElmer Life Sciences, Inc. (Boston, Mass.) and $^{125}$I-labeled I-TAC was obtained from Amersham Pharmacia Biotech (Buckinghamshire, UK). Monoclonal antibodies used in flow cytometry and ligand binding competition were from R&D Systems (Minneapolis, Minn.): anti-CXCR4 clones 12G5, 44708.111 (171), 44716.111 (172), 44717.111 (173), nmIgG2a, and nmIgG2b. The secondary anitbody, goat anti-mouse IgG PE conjugate (Coulter Immunotech, Miami, Fla.), was used to detect antibody binding by flow cytometry. The following cell lines were obtained from the American Type Culture Collection (Manassas, Va.): MCF-7 (adenocarcinoma; mammary gland), MDA MB-231 (adenocarcinoma; mammary gland), MDA MB-435s (ductal carcinoma; mammary gland), DU 4475 (mammary gland), ZR 75-1 (ductal carcinoma; mammary gland) and HEK 293 (human embryonic kidney). CEM-NKr (acute lymphoblastic leukemia; peripheral blood; T lymphoblast) cells were obtained from the NIH AIDS Research and Reference Reagent Program. Cell lines were cultured in DMEM (Mediatech, Herndon, Va.) supplemented with 10% fetal bovine serum (FBS) (HyClone Logan, Utah) at 37° C. in a humidified incubator at a 5% $CO_2$/air mixture. Human peripheral blood mononuclear cells (PBMC) were obtained from buffy coats of healthy donors (Stanford Blood Center, Palo Alto, Calif.) by centrifugation on Ficoll-Hypaque density gradients. Isolated PBMC were activated with 2.5 ug/ml phytohemagglutnin (PHA) (Sigma Chemical Company, St. Louis, Mo.) and 10 ng/ml recombinant human IL-2 (R&D Systems, Minneapolis, Minn.) for 3 days in RPMI-1640 (Mediatech, Herndon, Va.) supplemented with 10% FBS at 37° C. in a humidified incubator at a 5% $CO_2$/air mixture. After activation, the cells were washed and cultured in RPMI supplemented with 10% FBS and 10 ng/ml IL-2, which was replenished every 3-4 days until the day cells were used.

Binding Analysis. We employed our technique, Displace-Max, to examine the global profile of chemokine ligand interaction with CXCR4 on MCF-7 and CEM-NKr cells. This technology employs expanded, efficiency-maximized radioligand binding using filtration protocols as described previously (Kledal T N, et al. Science 277:1656-1659 (1997); Dairaghi, et al. *J Biol Chem* 274:21569-74 (1999); Gosling, J. et al. *J Immunol* 164:2851-6 (2000)). In these assays, DisplaceMax employed the simultaneous interrogation of MCF-7 or CEM-NKr cells, as indicated, by >110 distinct purified chemokines in the ability to displace $^{125}$I radiolabeled SDF-1α or I-TAC, as indicated, using the protocol described (Dairaghi, ET AL. *J Biol Chem* 274:21569-74 (1999); Gosling, J. et al. *J Immunol* 164:2851-6 (2000)). Briefly, chemokine elements were incubated with cells followed by the addition of radiolabeled chemokine ($^{125}$I SDF-1a or $^{125}$Ih I-TAC) for 3 hr at 4° C. in the following binding medium (25 mM HEPES, 140 mM NaCl, 1 mM $CaCl_2$, 5 mM $MgCl_2$ and 0.2% bovine serum albumin, adjusted to pH 7.1). Where indicated, anti-CXCR4 antibodies or isotype controls were included in the binding reactions. In these experiments cells were pre-incubated with the indicated concentration of antibody for 30 min at 4° C. prior to the addition of radiolabeled chemokine. Small molecules were included in some assays, where indicated. In these assays the compound was added to the plate to the indicated concentration followed by the addition of radiolabeled chemokine. All assays were then incubated for 3 hrs at 4° C. with gentle agitation. Following incubation in all binding assays, reactions were aspirated onto PEI-treated GF/B glass filters (Packard) using a cell harvester (Packard) and washed twice (25 mM HEPES, 500 mM NaCl, 1 mM $CaCl_2$, 5 mM $MgCl_2$, adjusted to pH 7.1). Scintillant (MicroScint 10, Packard) was added to the wells, and the filters were counted in a Packard Topcount scintillation counter. Data were analyzed and plotted using Prism (Graph-Pad Prism version 3.0a for Macintosh, GraphPad Software).

Determination of $^{125}$I SDF-1α Receptor Binding. Using the filtration based assay described above, cells were pre-incubated with either 1) buffer alone, 2) excess SDF-1β (90 nM final) or 3) MIG (175 nM final) as indicated for 30 min at 4° C. Following this incubation the indicated cold chemokine competitor at stated concentrations and $^{125}$I h I-TAC were added to the binding reactions. All assays were then incubated, harvested and analyzed as described above.

RT PCR. mRNA was isolated from cells using standard techniques. Complementary DNA was analyzed for the expression of CXCR3 and CXCR4 by PCR. Specific primers were obtained from Integrated DNA Technologies (Coralville, Iowa). Specific PCR products were measured by means of a Hybaid Omn-E (E&K Scientific Products, Inc., Saratoga, Calif.) during 35 cylces. GAPDH was measured as a control.

Invasion Assay. Invasion assays were performed as per the manufacturer's instructions. Briefly, chemokines were diluted in HBSS (Life Technologies, Gaithersburg, Md.) supplemented with 0.1% bovine albumin (Sigma Chemical Company, St. Louis, Mo.) and added to the lower wells of BD BioCoat Matrigel Invasion chambers (BD Biosciences, Bedford, Mass.). MDA MB-231 cells were added to the matrigel coated inserts and the plates were incubated at 37° C. in a humidified incubator at a 5% $CO_2$/air mixture for 22 hrs. Following this incubation, the inserts were transferred to a new plate and the media in the inserts was removed. Using a cotton swab the matrigel plug was removed from each well. The filters were then stained using Protocol Hema staining system (Biochemical Sciences, Inc., Swedesboro, N.J.). Invading cells were examined under a Nikon Elipse E800 (Nikon, Inc., Melville, N.Y.) microscope with a 40× lens. Cells were counted in 5 fields of view of each filter. Data represent the mean of 5 fields of view from each filter tested in triplicate.

Results

Recent reports have identified CXCR4 expression on several tumor cell types (Sehgal, et al., *J Surg Oncol* 69:99-104 (1998); Sehgal, A., et al. *J Surg Oncol* 69:239-48 (1998); Burger, et al. *Blood* 94:3658-67 (1999); Rempel, et al. *Clin Cancer Res* 6:102-11 (2000); Koshiba, T. et al. *Clin Cancer Res* 6:3530-5 (2000); Muller, A. et al. *Nature* 410:50-6 (2001); Robledo, et al. *J Biol Chem* 276:45098-45105 (2001)) and in one example link this expression with breast tumor cell metastasis (Muller, A. et al. *Nature* 410:50-6 (2001)). To further investigate the role of chemokine receptors on tumor cells we undertook to evaluate the expression of CXCR4 on several human breast tumor cell lines. Initially the pattern of CXCR4 expression was evaluated by flow cytometry. Primary IL-2 cultured T lymphocytes and two T cell lines, CEM-NKr and Jurkat, were examined to determine the T cell phenotype of anti-CXCR4 staining. Three breast tumor cell lines, MCF-7, MDA MB-231 and MDA MB-435s, were also tested (FIG. 1,a). All four anti-CXCR4 clones tested stained T cells. Surprisingly, while breast tumor cells are reported to express CXCR4, the widely used clone 12G5 did not detect any CXCR4 on the breast tumor cells. Weak and variable reactivity was detected with the three other clones tested on the breast tumor cells. The breast tumor cell lines DU 4475 and ZR 75-1 were also tested in this assay (data not shown) and found to have similar antibody staining profiles to the other breast tumor cells tested. Thus, the staining patterns of the mAb panel for CXCR4 seem to suggest two distinct types of reactivity: a "leukocyte" CXCR4 phenotype (exemplified by CEM-NKr, Jurkat and IL-2 lymphocyte staining) and a breast tumor cell phenotype (exemplified by weak staining on MCF-7 and MDA MB-231 breast tumor cell lines).

The consistent lack of reactivity using the most widely employed anti-CXCR4 mAb, clone 12G5, on breast tumor cells led us to examine CXCR4 expression in these cells by RT PCR. mRNA was isolated from the three breast tumor lines tested in flow cytometry as well as IL-2 cultured lymphocytes and the T cell lines, CEM-NKr and Jurkat, as positive controls for CXCR4 expression. Despite the lack of reactivity with 12G5 and the variable reactivity with the other anti-CXCR4 clones tested, the breast tumor cell lines, MCF-7 and MDA MB-231, did express CXCR4 message; however, MDA MB-435s was found to be negative for CXCR4 expression. In all cases GAPDH was measured as a control. To examine whether differences in mAb reactivity may be due to sequence differences thus resulting in epitope variations in CXCR4 on various cell lines, we then sequenced the PCR products generated from MCF-7, as a representative CXCR4+ breast tumor cell, and CEM-NKr, as a representative T cell. The sequences from these two cell lines are identical to published CXCR4 sequences suggesting that despite the different CXCR4 antibody profiles, the genetic and thus the polypeptide structure of CXCR4 in both cell types was identical.

We have previously reported a set of techniques by which receptor binding to a comprehensive array of chemokine ligands can be simultaneously assessed (Dairaghi, et al. *J Biol Chem* 274:21569-74 (1999); Gosling, J. et al. *J Immunol* 164:2851-6 (2000)). In this fashion we probed the CXCR4 binding profile on CEM-NKr as compared to MCF-7 cells. Greater than 90 chemokine elements were tested for the ability to displace the signature chemokine, $^{125}$I SDF-1α, for binding to CEM-NKr (FIG. 2) or MCF-7 cells (FIG. 2). As expected, the potential high affinity competitors of $^{125}$I SDF-1α on CEM-NKr include hSDF-1β and mSDF-1, while hSDF-1α and HHV8 vMIP-II exhibit potential moderate affinity competition. This is consistent with all previously reported results of SDF-1 as the only non-viral ligand for CXCR4. However, the overall pattern of competition on MCF-7 cells was markedly different. In this cell type hI-TAC and mI-TAC demonstrated high affinity competition for the same signature ligand SDF-1. To further investigate this unusual result $^{125}$I I-TAC was tested as the signature ligand on MCF-7 cells (FIG. 2). The high affinity displacement profile using $^{125}$I I-TAC on MCF-7 was identical to the profile obtained using $^{125}$I SDF-1α. Thus, on MCF-7 cells I-TAC and SDF-1 behave indistinguishably in binding and compete for the same receptor site.

Figure 3:
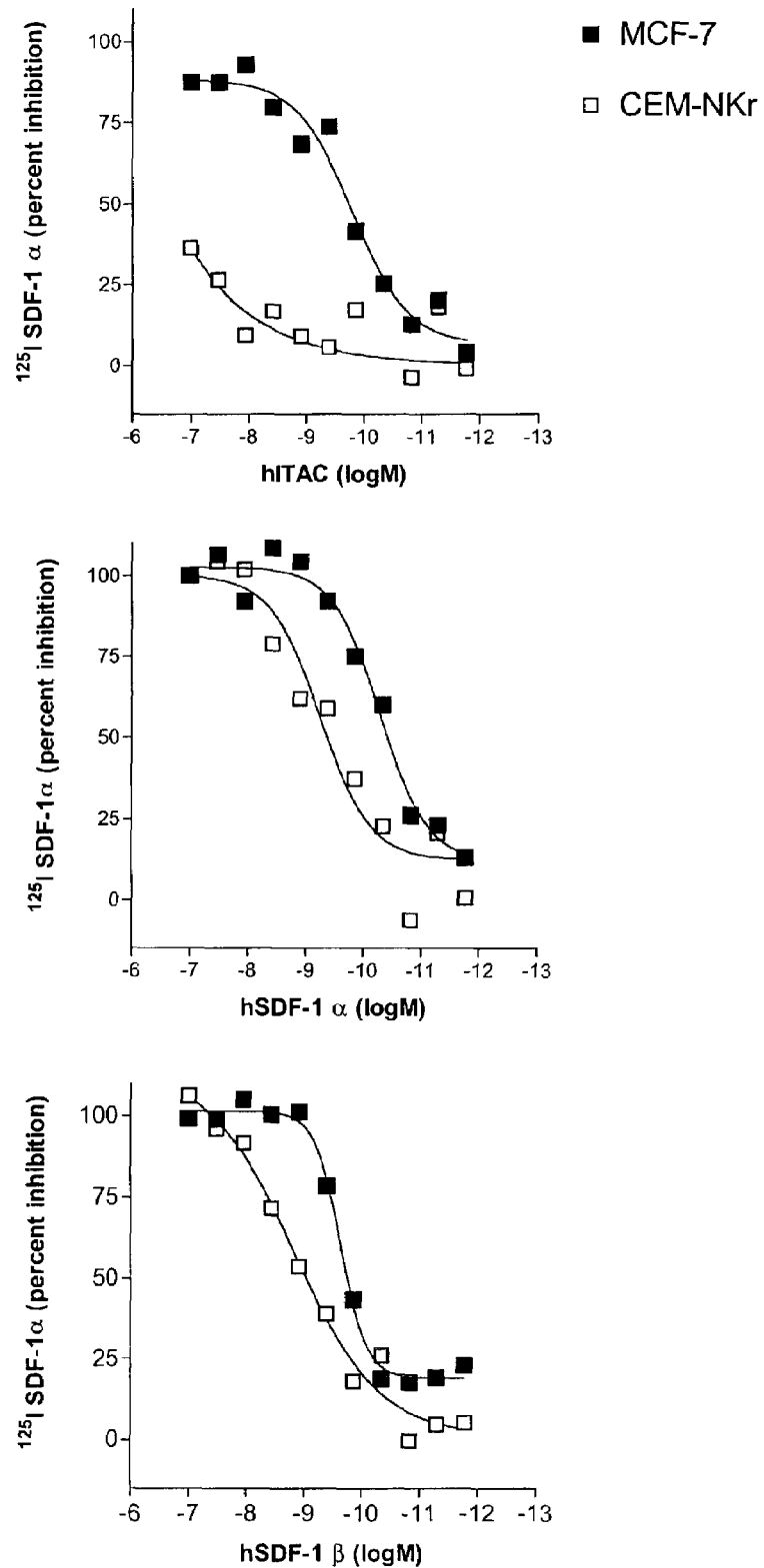
FIG. 3 illustrates a comparison of ligand binding affinity and specificity on CEM-NKr and MCF-7. Selected potential high affinity ligands identified in FIG. 1 were chosen for dose response competition on CEN-NKr (open squares) and MCF-7 (solid squares). In each competition $^{125}$I SDF-1α is in competition with a cold competitor chemokine as indicated.

To characterize further the binding of I-TAC and SDF-1, dose response curves were obtained in competition binding experiments with selected potential high affinity ligands on CEM-NKr and MCF-7. As suggested by the DisplaceMax data, I-TAC does compete with $^{125}$I SDF-1α for binding to MCF-7, but not CEM-NKr (FIG. 3). Homologous competition of $^{125}$I SDF-1α with either SDF-1 isoform, SDF-1α or SDF-1 β, resulted in complete competition on CEM-NKr and MCF-7 (FIG. 3). Notably, the affinity of SDF-1 for the receptor expressed on MCF-7 is higher than that on CEM-NKr. Thus, while the sequence of CXCR4 is identical in both cell types the ligand binding specificity and affinity differ on T cells vs. breast tumor cells.

Figure 4:
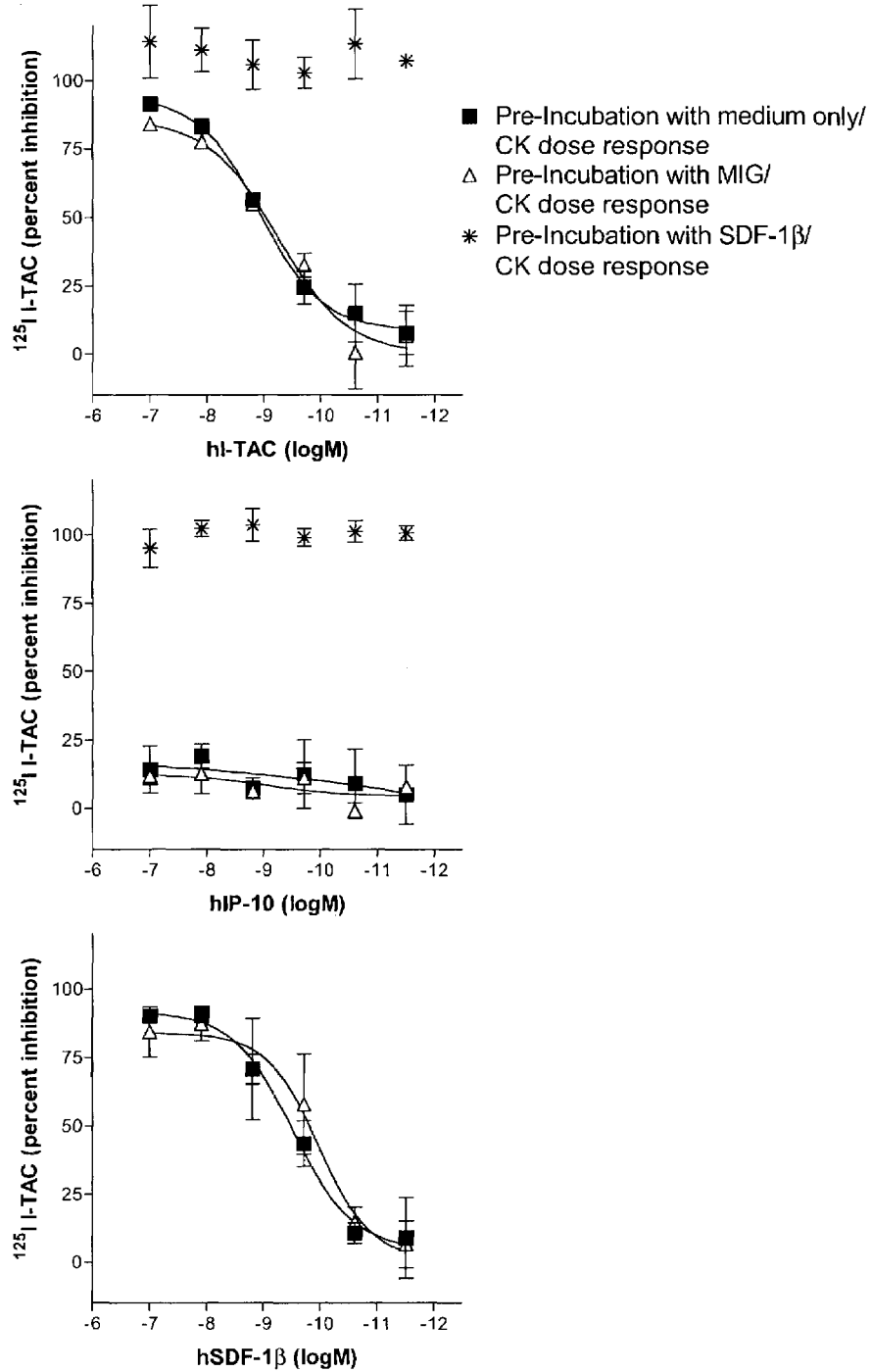
FIG. 4 illustrates $^{125}$II-TAC binding on MCF-7 cells is not due to a classic CXCR3 binding interaction. The ability of $^{125}$I-TAC to compete with the indicated chemokines was examined in the presence of buffer only (solid squares), excess MIG (to inhibit any CXCR3-mediated binding; open triangles), or excess SDF-1α (to inhibit any CXCR4-mediated binding; asterisks).

We next investigated whether the I-TAC binding detected on MCF-7 cells was CXCR4-mediated or CXCR3-mediated since CXCR3 has long been established as the principal receptor for I-TAC (Cole, K. E. et al. *J Exp Med* 187:2009-21. (1998)). To this end, $^{125}$I I-TAC binding was examined under conditions that would inhibit 'classic' CXCR3 mediated binding (i.e. binding of the reported CXCR3 ligands MIG, I-TAC and IP-10 to CXCR3) thus permitting 'classic' CXCR4 mediated binding (i.e. binding of the reported CXCR4 ligand SDF-1 to CXCR4), as well as the converse situation. MCF-7 cells were pre-incubated with either medium alone, medium containing excess MIG (~175 nM; to inhibit CXCR3-mediated binding) or medium containing excess SDF-1β (~90 nM; to inhibit CXCR4-mediated binding). I-TAC competed with $^{125}$I I-TAC for binding to the MCF-7 cells with an IC50 of 1 nM (FIG. 4,*a*) confirming that it is a high affinity ligand for this receptor on these cells. Similarly, cells first pre-incubated with excess MIG were then still able to give the same homologous I-TAC/$^{125}$I I-TAC binding curve again with an IC50 of 1 nM (FIG. 4). However, when cells were first pre-treated with excess SDF-1β all $^{125}$I I-TAC binding was inhibited (FIG. 4) suggesting that the observed $^{125}$I I-TAC binding on breast tumor cells is CXCR4-mediated. $^{125}$I I-TAC binding to MCF-7 cells was not inhibited when IP-10 was tested as the cold chemokine competitor. Again, pre-incubation with excess MIG did not effect this binding profile; however pre-incubation of the cells with SDF-1β completely inhibited $^{125}$I I-TAC binding. When the CXCR3 ligand MIG was tested as the cold competitor $^{125}$I I-TAC binding to the cell was not inhibited (data not shown). As expected from the DisplaceMax data represented in FIG. 1, SDF-1β competed with $^{125}$I I-TAC for binding to these cells with high affinity (IC50 of 1 nM). Pre-incubation of cells with excess MIG did not effect the SDF-1β/$^{125}$I I-TAC competition, again suggesting the binding detected is mediated by CXCR4 and not CXCR3. Thus, the preponderance of the data suggest overwhelmingly that the novel binding profile detected on MCF-7 cells is due to the action of CXCR4 (or a CXCR4-like molecule) and not CXCR3.

This hypothesis was examined further by PCR. Isolated mRNA used previously (see above) was used to probe for evidence of CXCR3 transcripts. While, IL-2 cultured lymphocytes expressed CXCR3; no other cell tested expressed CXCR3. The lack of detected CXCR3 expression by RT PCR supports data from FIG. 4, again suggesting that the I-TAC binding on MCF-7 cells is not CXCR3-mediated.

Figure 5:
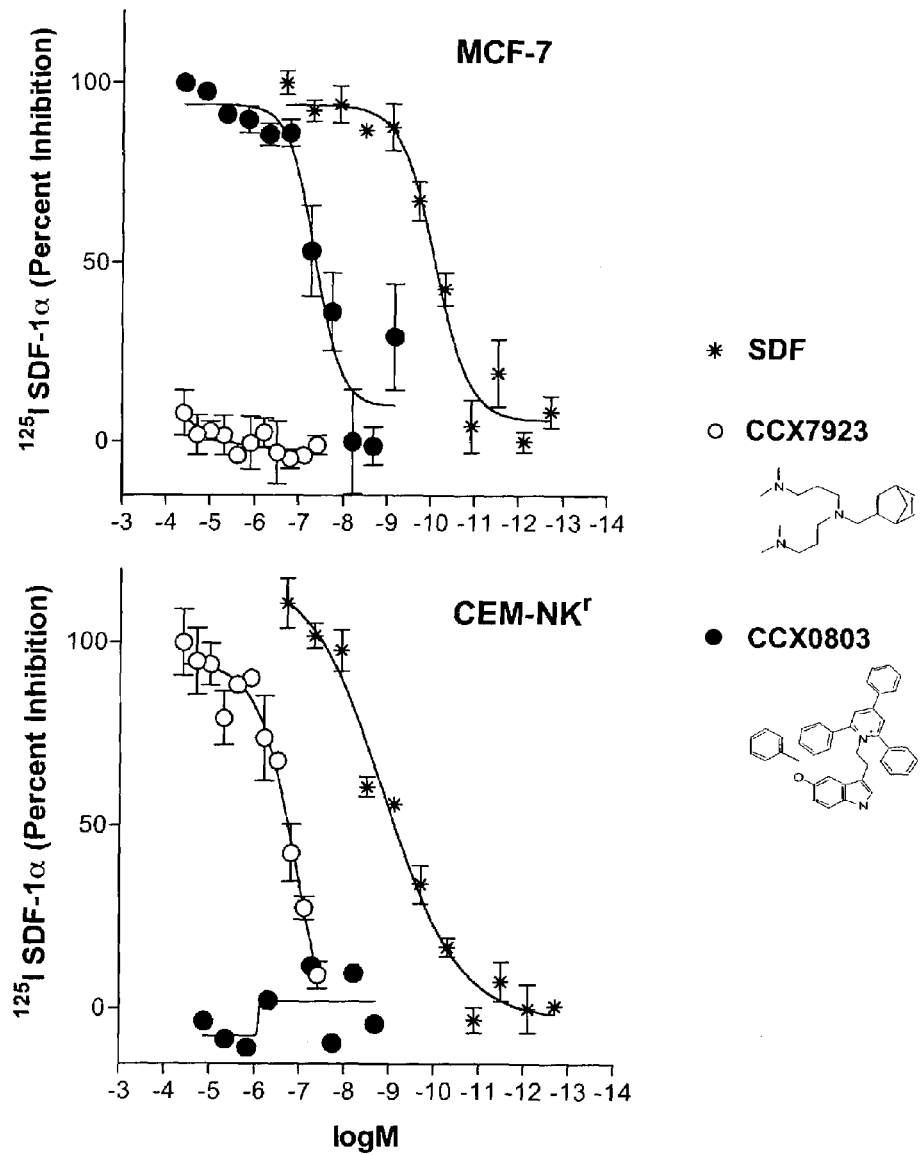
FIG. 5 illustrates competitive binding data. Two CXCR4 antagonists, CCX0803 (solid circles) and CCX7923 (open circles), compete specifically with $^{125}$I SDF-1α, on discrete cell types; no cross competition is detected. SDF-1α (asterisks) was also included as a cold competitor of $^{125}$I SDF-1α binding on both MCF-7 and CEM-NKr. Chemical structures of CCX0803 and CCX7923 are shown in the inset. The predicted IC50 values of SDF-1α and CXCR4 antagonist competition are provided in the accompanying table.

The nearly ubiquitous expression of CXCR4 is considered a significant obstacle in the effort to target this receptor with small molecular weight organic compound (SMC) therapeutics. Our results suggesting that the same protein sequence expressed in different cell types possessed (i) different antibody reactivity phenotypes; (ii) altered ligand affinity; and (iii) discrete ligand specificity, led us to search for SMC that might act as antagonists to the breast tumor cell form of CXCR4 but not the T cell form of CXCR4. We screened SMC (nearly 135,000) using two high throughput screens: one designed to assess the leukocyte form and one to probe the breast cancer form of CXCR4. The results of those screens indicated that clear pharmacologic discrimination of the two forms was possible (FIG. 5). For example, the small molecule designated CCX0803 competes with $^{125}$I SDF-1α for binding to MCF-7 with an IC50 of 46 nM (FIG. 5), however, this SMC does not inhibit $^{125}$I SDF-1α binding on CEM-NKr at all (FIG. 5). By contrast, a different SMC antagonist, CCX7923, inhibits $^{125}$I SDF-1α binding to CEM-NKr with an IC50 of 106 nM (FIG. 5,*b*), but does not inhibit $^{125}$I SDF-1α binding on MCF-7 cells (FIG. 5,*a*). These two compounds reveal the marked and unambiguous pattern of non-reciprocal binding inhibition of ligands to the two forms of CXCR4 differentially expressed on breast tumor lines vs. leukocytes. In conclusion, different cell types expressing identical protein sequences can be pharmacologically distinct, permitting a protein in a disease state (i.e. CXCR4 on breast tumor cells) to be distinguished from the same protein expressed on different CXCR4 bearing cells.

After initially determining that breast cancer cells exhibit a topology of CXCR4 which is distinct from the topology seen on other non-tumor or non-cancerous tissue further studies were undertaken. These phenotyping studies (using antibody reactivity, ligand binding profile and pharmacologic discrimination, see methods detailed herein), have clearly shown that many cancer (or tumor) cell types also exhibit the CXCR4 topology initially correlated with breast tumor cells. The following tumor cells were examined and exhibit the cancer-correlated CXCR4 topology: human ovarian carcinoma, human cervical adenocarcinoma, human Burkitt's lymphoma, human mammary adenocarcinoma, human mammary ductal carcinoma, human glioblastoma, and mouse mammary tumor.

Finally, the CXCR4 expressed on breast tumor cells is functional. In an invasion assay, SDF-1 induced cell invasion. Therefore, CXCR4 is not only expressed in these cells, but engagement by a ligand (SDF-1) is able to induce a signal through this receptor and cause cells to respond such that the cell is able to invade through a filter.

Tumors and other cancers are difficult to treat in part because of their rapid rate of cell growth. In this respect, tumors are known to share some growth characteristics with rapidly dividing early embryonic tissues. One school of thought suggests that tumors in the adult may represent 'revertants' to an embryonic growth phenotype. Both the SDF-1 and CXCR4 genetic knockout mice are embryonic lethal, suggesting that this ligand receptor pair is a critical component of growth and development. Approximately 50% of homozygous mutant SDF-1 embryos die perinatally by 18.5; the remaining homozygous littermates die within 1 hr of birth (Kishimoto, et al. Nature 382: 635-638 (1996)). Similarly, ~⅓ of the homozygous CXCR4 knock out mice die perinatally at E18.5 (Ma, et al PNAS 95:9448-9453 (1998)). In both the receptor and ligand knockouts defects in lymphopoiesis and myelopoiesis were observed. The fetal liver is the major site of hematopoiesis in the mouse at day 11 and continues as such until the first post-natal week. To this end we decided to examine the expression of the cancer-correlated topology of CXCR4 in this compartment. We examined CXCR4 expression on wildtype mouse embryos at E17 (a point in development close to the time the knockout animals die) and E13 (a point in development distinct from the time the knockout animals die, yet after hematopoiesis begins). In SDF-1 binding assays radiolabeled human-SDF-1 binds to E13 fetal liver cells and both SDF and I-TAC (mouse and human proteins) are able to compete with the radiolabeled tracer for binding. This altered ligand specificity as exemplified by I-TAC binding to the SDF-1 receptor is a hallmark of the topology of CXCR4 we first correlated with cancer cells. Furthermore, the pharmacological agents that interact with the cancer-associated topology are able to compete with SDF-1 binding to the E13 topology of CXCR4, yet the lymphocyte antagonists do not. As stated above, such pharmacologic distinction is another hallmark of the ability to detect different topologies of CXCR4. Later in development, the E17 fetal liver cells also express CXCR4, but these cells respond to SDF-1 by mobilizing intracellular calcium. CXCR4 antagonists to the 'lymphocyte' topology inhibit this SDF-1 mediated calcium mobilization however, CXCR4 tumor topology antagonists have no effect. Thus, these data suggest that while wildtype fetal liver cells at E13 and E17 both express CXCR4, the CXCR4 topology expressed at embryonic day E13 and E17 are different. Based on the binding studies, the CXCR4 topology expressed on E13 fetal liver cells is indistinguishable from the tumor-correlated topology while the CXCR4 topology expressed on E17 fetal liver cells is indistinguishable from the lymphocyte-correlated topology. Although the binding studies in embryonic mice models correlate well with data from human studies, preliminary experiments using mice which have a targeted disruption of the CXCR4 gene suggest that the SDF-1 and I-TAC binding profiles observed on embryonic day 13 (E13) fetal liver cells are unchanged. This may imply either that these experimental mice have remaining copies of the CXCR4 gene which were not successfully targeted, or that in mice the gene encoding the alternate topology is not identical the targeted version of CXCR4.

Experiments also demonstrate that the tumor-correlated form of CXCR4 can also provide a stimulatory signal to growing tumor cells. Tumor cells, which have a distinct topology of CXCR4, can upregulate certain genes involved in cell cycle or transcription in response to SDF-1 stimulation. More importantly, if tumor cells expressing the tumor correlated form of CXCR4 are starved of serum in culture overnight they begin to go through apoptosis (cell death). When SDF-1 is added to supplement these cultures the cells are able to recover from the starvation as compared to untreated controls. Thus SDF-1 CXCR4 therefore serves as an anti-apoptotic signal. Cancer cells are often characterized as cells that have lost the ability to undergo apoptosis.

Example 2

This example shows that CCR1 forms different topologies in different cells.

This example shows that CCR1 also forms naturally occurring distinct topologies in different cell types. This example further extends Example 1 to demonstrate that expression of the same gene in different cellular 'backgrounds' can produce surface chemokine receptor proteins with distinct topologies and properties. Thus, the existence of distinct receptor topologies on different cell types is not a result of differences in the gene, but rather of the cell type in which the gene product (protein) is expressed.

In addition to the data described above supporting the existence of pharmacomorphs of CXCR4, the existence of potential pharmacomorphs of other chemokine receptors was also investigated. In this section, data is presented that shows that CCR1 exhibits different topologies in different cell types. As with CXCR4, CCR1 exhibits markedly different antigenic reactivity as a function of the cell type in which CCR1 is expressed. Based on studies where a single cDNA construct is transfected into different cell types that do not express endogenous CCR1, it is shown here that the expression of an identical CCR1 genetic sequence can yield protein products which are antigenically distinct from one another (as determined by reactivity with a panel of monoclonal antibodies), and which recapitulates in part the topology profile seen in 'native' cell lines and primary cells. As is the case with the CXCR4 topology, the CCR1 topologies not only exhibit discrete antigenic reactivity, but also altered ligand binding (both in terms of specificity and affinity), and altered cellular function (e.g. $Ca^{2+}$ signaling and migration properties). Thus, CCR1 serves as another example of a chemokine receptor displaying different topologies, providing more evidence demonstrating the ability of genetically identical sequences expressed in different cell types to exhibit different cellular effects and pharmacologic profiles.

Antibody Reactivity Phenotype

Different expressed protein topologies adopted by a given receptor gene may exhibit different staining profiles in response to a panel of antibodies (such as monoclonal antibodies raised against recombinant proteins representing the receptor polypeptide) on different cell types. This is the case with the chemokine receptor CCR1. Five different monoclonal antibodies (designated clones #1-5) react differently with different cell types despite the fact that all cells tested express the CCR1 receptor. See FIG. 6. For example, Clones #5 and #2 recognizes CCR1 expressed on transfectants (HEK-293 and NSO-CCR1), THP-1 cells (acute monocytic leukemia), immature dendritic cells (DC) and neutrophils, but not monocytes. Clone #4 recognizes CCR1 on transfectants and THP-1 cells, but not on primary cells tested (monocytes, neutrophils or immature DC). Thus, antibodies directed against the same protein (CCR1) exhibit different patterns of recognition dependent upon the cell type in which CCR1 is expressed.

Ligand Binding

Chemokine receptor topologies encoded by a given receptor gene may vary in their ligand binding profile. They may have differing ligand binding 'fingerprints' (i.e., they to bind a different spectrum of discrete ligands). Additionally, they may bind ligands within their fingerprint with different affinities on different topologies. This is the case with several CCR1 ligands. Two alternatively spliced forms of the human CC chemokine CCL23, CKβ8 and CKβ8-1, have been reported. CKβ8 is the 99-amino acid form (amino acids 1-99) of CCL23, while the alternatively spliced variant, CKβ8-1, consists of amino acids 1-116. Both mature forms have been assigned as functional ligands for CCR1. Two $NH_2$-terminal truncation variants of CKβ8 (24-99 and 25-99) have been described and shown to be much more potent than the mature form of CKβ8 on CCR1. Here we focus on the biological activity of two of these CKβ8 forms, CKβ8 (1-99) and CKβ8 (25-99), as well as two other CCR1 ligands, MIP-1α and leukotactin. See. FIG. 7. For example, in a $^{125}I$ MIP-1α and CKβ8 (1-99) competition on HEK293-CCR1 cells, the calculated IC50 is 64 nM. However, this same competition on NSO-CCR1 cells results in a calculated IC50 of 3.9 nM. Thus the same chemokines competing for binding to the same protein (CCR1) on different cell types produce vastly different binding characteristics.

Function

Based on their topology, chemokine receptors control or impart different biological functions in different cellular or pathophysiological contexts. They differentially control a function (e.g., cell migration) by possessing different ligand binding fingerprints in different cellular contexts. They differentially control cellular functions by differential coupling and second messenger signaling in different cellular contexts (such as by linking to different G proteins, etc.). CCR1 topologies exhibit an example of this phenomenon.

For example, ligand (i.e. CKβ8(1-99)) binding to CCR1 expressed on neutrophils does not induce cell migration. However, the same ligand (CKβ8(1-99)) can induce CCR1 mediated cell migration on THP-1 cells, monocytes and immature DC. See, FIG. 8.

Furthermore, the same CCR1 ligands induce Ca2+ mobilization signals in different cells to different extents. For example, the CCR1 ligands CKβ8 (1-99), CKβ8 (25-99), Leukotactin, MIP-1α and mMIP-1γ are able to mobilize Ca2+ in HEK293-CCR1, THP-1 and monocytes; however these same ligands do not mobilize Ca2+ in neutrophils despite the fact that CCR1 is expressed in these cells. See, FIG. 9.

Genetic Identity

Topologies of a given receptor share a polypeptide backbone that is identical or very similar in amino acid sequence; genetically the sequences are identical. The cDNA encoding the CCR1 protein was transfected into two different cell types, HEK293 and Jurkat. The transfectants exhibited different antibody reactivity despite the fact that they expressed genetically identical CCR1. See, FIG. 10.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of identifying a cancer cell having a chemokine receptor, wherein the cell is from a tissue, the method comprising
    contacting the cell with I-TAC and SDF-1; and
    determining whether I-TAC and SDF-1 compete with each other for binding on the chemokine receptor, wherein competition for binding indicates the presence of a cancer cell.

2. The method of claim 1, wherein the identified cancer cell is selected from the group consisting of a breast cancer cell, an ovarian cancer cell, cervical cancer cell, a Burkitt's lymphoma cell and a glioblastoma cell.

* * * * *

SEQUENCE LISTING

```
<160> NUMBER OF SEQ ID NOS: 4

<210> SEQ ID NO 1
<211> LENGTH: 352
<212> TYPE: PRT
<213> ORGANISM: Homo sapiens
<220> FEATURE:
<223> OTHER INFORMATION: CXCR4 chemokine receptor

<400> SEQUENCE: 1

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270
```

```
Gly Cys Glu Phe Glu Asn Thr Val His Lys Trp Ile Ser Ile Thr Glu
            275                 280                 285

Ala Leu Ala Phe Phe His Cys Cys Leu Asn Pro Ile Leu Tyr Ala Phe
        290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 2
<211> LENGTH: 355
<212> TYPE: PRT
<213> ORGANISM: Homo sapiens
<220> FEATURE:
<223> OTHER INFORMATION: CCR1 chemokine receptor

<400> SEQUENCE: 2

Met Glu Thr Pro Asn Thr Thr Glu Asp Tyr Asp Thr Thr Thr Glu Phe
1               5                   10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
        35                  40                  45

Leu Val Gly Asn Ile Leu Val Val Leu Val Leu Val Gln Tyr Lys Arg
    50                  55                  60

Leu Lys Asn Met Thr Ser Ile Tyr Leu Leu Asn Leu Ala Ile Ser Asp
65                  70                  75                  80

Leu Leu Phe Leu Phe Thr Leu Pro Phe Trp Ile Asp Tyr Lys Leu Lys
                85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Ile Ile Trp Ala Leu
145                 150                 155                 160

Ala Ile Leu Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
        195                 200                 205

Val Leu Pro Leu Leu Val Met Ile Ile Cys Tyr Thr Gly Ile Ile Lys
    210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
                245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
        275                 280                 285
```

```
Ile Ala Tyr Thr His Cys Cys Val Asn Pro Val Ile Tyr Ala Phe Val
    290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                325                 330                 335

Glu Arg Val Ser Ser Thr Ser Pro Ser Thr Gly Glu His Glu Leu Ser
                340                 345                 350

Ala Gly Phe
        355

<210> SEQ ID NO 3
<211> LENGTH: 200
<212> TYPE: PRT
<213> ORGANISM: Artificial Sequence
<220> FEATURE:
<223> OTHER INFORMATION: Description of Artificial Sequence:poly Gly
      flexible linker
<220> FEATURE:
<221> NAME/KEY: MOD_RES
<222> LOCATION: (6)..(200)
<223> OTHER INFORMATION: Gly at positions 6-200 may be present or absent

<400> SEQUENCE: 3

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
                20                  25                  30

Gly Gly Gly Gly Gly Gly Gly Gly Gly Gly Gly Gly Gly Gly Gly Gly
            35                  40                  45

Gly Gly Gly Gly Gly Gly Gly Gly Gly Gly Gly Gly Gly Gly Gly Gly
        50                  55                  60

Gly Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Gly Gly Gly Gly Gly Gly Gly Gly
        195                 200

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:chemokine
      receptor second extracellular loop common structural feature
```

-continued

```
<400> SEQUENCE: 4

Asp Arg Tyr Leu Ala Ile Val His Ala
1               5
```